United States Patent [19]  
Fujikura et al.

[11] Patent Number: 4,727,082  
[45] Date of Patent: Feb. 23, 1988

[54] DIHYDROPYRIDINE COMPOUNDS AND PHARMACEUTICAL COMPOSITIONS CONTAINING THEM

[75] Inventors: Takashi Fujikura; Noriki Ito, both of Saitama; Yuzo Matsumoto, Tokyo; Yasuo Isomura, Tokyo; Masaharu Asano, Tokyo; Toichi Takenaka, Tokyo, all of Japan

[73] Assignee: Yamanouchi Pharmaceutical Co., Ltd., Tokyo, Japan

[21] Appl. No.: 908,350

[22] Filed: Sep. 17, 1986

[30] Foreign Application Priority Data

Jun. 28, 1984 [JP] Japan ............... 59-133650

[51] Int. Cl.$^4$ ............... A61K 31/455; C07D 211/90
[52] U.S. Cl. ............................. 514/356; 546/321
[58] Field of Search ...................... 546/321; 514/356

[56] References Cited

U.S. PATENT DOCUMENTS 4,492,703  1/1985  Goldmann et al. ............... 546/321
4,500,527  2/1985  Loev et al. ............... 546/321

OTHER PUBLICATIONS

Baldwin, J. J. et al., J. Med. Chem. 24, (1981), pp. 628–631.

Primary Examiner—Alan L. Rotman  
Assistant Examiner—Dale A. Bjorkman  
Attorney, Agent, or Firm—Burgess, Ryan & Wayne

[57] ABSTRACT

A dihydropyridine compound of the following general formula (I) or a salt thereof:

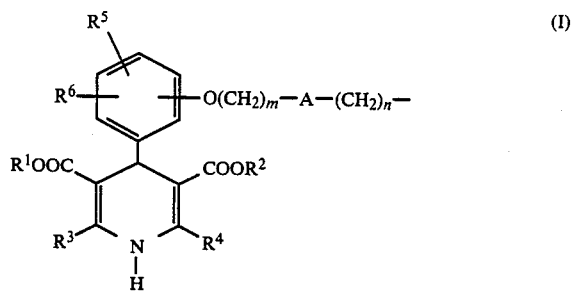

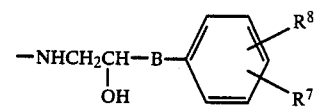

wherein $R^1$ and $R^2$, which are the same or different, each represents a $C_1$ to $C_{10}$ alkyl group, a lower alkyl group which is interrupted by oxygen atom(s), or a lower alkyl group substituted by $C_3$ to $C_6$ alicyclic group(s); $R^3$ and $R^4$, which are the same or different, each represents a lower alkyl group; $R^5$ and $R^6$, which are the same or different, each represents a hydrogen atom, a nitro group, a halogen atom, a lower alkyl group, a lower alkoxy group, a lower alkylthio group, a lower alkylsulfonyl group, or a lower alkylsulfinyl group; $R^7$ and $R^8$, which are the same or different, each represents a hydrogen atom, a halogen atom, a cyano group, a lower alkoxy group, or a lower alkanoylamino group, or $R^7$ may combine with $R^8$ to form a naphthyl group together with the adjacent phenyl group; A represents a single bond, a vinylene group (—CH=CH—), or a ethynylene group (—C≡C—); B represents a single bond or —CH$_2$O—; and m and n, which are the same or different, each represents 0 or an integer of 1 to 5.

The compounds are useful for the treatment of various cardiovascular disorders, since they possess both Ca$^{2+}$-antagonistic and adrenergic beta-receptor blocking activities.

10 Claims, No Drawings

DIHYDROPYRIDINE COMPOUNDS AND PHARMACEUTICAL COMPOSITIONS CONTAINING THEM

It is known that certain dihydropyridine derivatives have a $Ca^{2+}$-antagonistic action, and are highly useful for the treatment of various cardiovascular disorders such as angina pectoris, myocardial infarction, hypertension and cardiac arrythmia. It is further known that beta-adrenoceptor blocking agents are also useful for the treatment of such cardiovascular disorders.

However, the mechanism of action of dihydropyridine derivatives is entirely different from that of beta-adrenoceptor blocking agents. Beta-adrenoceptor blocking agents reduce heart rate, cardiac output, stroke volume, cardiac work and myocardial oxygen demand, whereas $Ca^{2+}$-antagonists improve left ventricular function due to their coronary vasodilating and systemic vasodilating effect (reduction in afterload) and also inhibit coronary vasospasm.

Recently it has been reported that a combined administration of a $Ca^{2+}$-antagonist and a beta-blocker can achieve maximal symptomatic improvement in clinical angina pectoris. [Bassan, M., Weiler-Ravell, D. and Shalev, O.; Additive antianginal effect of verapamil in patients receiving propranolol; Br. Med. J., 284, 1067 (1982)]. Further it has been reported that a combined administration of such two kinds of drug can be recommended for the treatment of hypertension, since the side effects of either drug are almost abolished or inhibited by the combined administration of both drugs; beta-blocker inhibits $Ca^{2+}$-antagonist-induced reflex increase of heart rate and completely inhibits $Ca^{2+}$-antagonist-induced increases of plasma renin activity. [Acki, A., Kondo, S., Mochizuki, A., et al; Antihypertensive effect of Cardiovascular $Ca^{2+}$-antagonist in hypertensive patients in the absence and pressure of beta-adrenergic blockade; Am. Heart J., 96, 218 (1978)]

Thus, it would be expected that a compound having both $Ca^{2+}$-antagonistic and beta-blocking activities is of interest in the management of ischemic heart-diseases and hypertension. In particular, it would be expected that beta-blocking activity is heart-selective, that is, cardiac $beta_1$-adrenoceptor blocking activity for the above clinical fields. This invention provides novel compounds which have both these actions (namely, $Ca^{2+}$-antagonistic activity and adrenergic beta-receptor blocking activity), and production methods for the compounds; the invention provides some novel compounds which have $Ca^{2+}$-antagonistic activity and cardiac $beta_1$-adrenoceptor blocking activity.

The compounds of this invention are those of the general formula (I) and salts thereof:

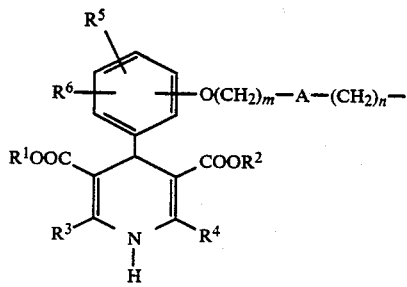

(I)

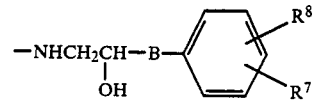

-continued wherein $R^1$ and $R^2$ are the same or different and selected from a $C_1$ to $C_{10}$ alkyl group, lower alkyl groups interrupted by oxygen atom(s), and lower alkyl groups substituted by $C_3$ to $C_6$ alicyclic group(s); $R^3$ and $R^4$ are the same or different lower alkyl groups; $R^5$ and $R^6$ are the same or different and selected from hydrogen and halogen atoms and nitro, lower alkyl, lower alkoxy, lower alkylthio, lower alkylsulfonyl and lower alkylsulfinyl groups; $R^7$ and $R^8$ are the same or different and are selected from hydrogen and halogen atoms and cyano, lower alkoxy and lower alkanoylamino groups or combine to form with the adjacent phenyl group, a naphthyl group; A represents a single bond, or a vinylene (—CH=CH—) or ethynylene group (—C≡C—); B represents a single bond or —CH$_2$O—; and m and n are the same or different and selected from O and integers of 1 to 5.

The above symbols have the same meaning wherever used hereinafter.

This invention also relates to the production of these compounds, and to pharmaceutical compositions containing them.

Unexamined German Patent Publication No. 3207982 and Belgian Pat. No. 893984 disclose certain dihydropyridine compounds. The former discloses dihydropyridine compounds wherein the 4-position phenyl group has an alkyl group, a nitro group, an alkoxy group, and/or —X$_1$—B$_1$—Y$_1$ (wherein X$_1$ is an oxygen atom, B$_1$ is an alkylene group, and Y$_1$ is a phenyl group substituted by a halogen atom or an alkyl group).

The latter discloses dihydropyridine compounds wherein the 4-phenyl group has a nitro group, a phenylalkylthio group, and/or a phenylalkoxy group.

The compounds of this invention have entirely different chemical structures from those of the abovementioned prior art compounds, and show unique pharmacological effects since they possess both $Ca^{2+}$-antagonistic and adrenergic beta-receptor blocking activities. In addition, some of the compounds of this invention also have other advantageous pharmacological actions such as cardiac $beta_1$-adrenoceptor blocking activity, intrinsic symphathomimetic activity and/or alpha-adrenoceptor blocking activity.

The term "lower" in the foregoing definitions means a straight or branched carbon chain having 1 to 5 carbon atoms. Thus examples of the "lower alkyl" are methyl, ethyl, propyl, iso-propyl, butyl, isobutyl, sec-butyl, tert-butyl, pentyl (amyl), isopentyl, tert-pentyl, neopentyl, 1-methylbutyl, 2-methylbutyl, 1,2-dimethylpropyl, 1-ethylpropyl.

Examples of the "lower alkoxy" are methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 2-methylbutoxy, 1,2-dimethylpropoxy, 1-ethylpropoxy. Examples of "lower alkylthio" are methylthio, ethylthio, propylthio, isopropylthio, butylthio, sec-butylthio, tert-butylthio, pentylthio, neopentylthio, 2-methylbutylthio, 1,2-dimethylpropylthio, 1-ethylpropylthio. Examples of "lower alkylsulfonyl" are methylsulfonyl, ethylsulfonyl, propylsulfonyl, butylsulfonyl, isobutylsulfonyl, pentylsulfonyl; and examples of "lower alkylsulfinyl" are methylsulfinyl, ethylsulfinyl, propylsulfinyl, butylsulfinyl, isobutylsulfinyl, pentylsulfinyl. Examples of "lower alkyl substituted by $C_3$ to $C_6$ alicyclic group(s) "are cyclopropyl lower alkyl, cyclobutyl lower alkyl, cyclopentyl lower alkyl, cyclohexyl lower alkyl. Thus "$C_3$ to $C_6$ alicyclic group" means cycloalkyl of 3 to 6 C atoms; the lower alkyl may be substituted at any position(s) by the $C_3$ to $C_6$ alicyclic group(s). Examples of "lower alkanoylamino" are acetylamino, propionylamino, butyrylamino, isobutyrylamino, valerylamino, isovalerylamino, pivaloylamino. As examples of "lower alkyl which is interrupted by oxygen atom(s) there are methoxymethyl, 1-methoxyethyl, 2-methoxyethyl, 1-methoxypropyl, 2-methoxypropyl, 3-methoxypropyl, 1-methoxy-1-methylethyl, 2-methoxy-1-methylethyl, 1-methoxybutyl, 2-methoxybutyl, 3-methoxybutyl, 4-methoxybutyl, 3-methoxyl-1-methylpropyl, ethoxymethyl, 1-ethoxyethyl, 2-ethoxyethyl, 1-ethoxypropyl, 2-ethoxypropyl, 3-ethoxypropyl, propoxymethyl, isopropoxymethyl, 1-propoxyethyl, 1-isopropoxyethyl, 2-propoxyethyl, 2-isopropoxyethyl. As examples of "$C_1$ to $C_{10}$ alkyl" in the foregoing definitions for $R^1$ and $R_2$, there are the above-mentioned lower alkyl, and other alkyls such as hexyl, isohexyl, 1-methylpentyl, 2-methylpentyl, 3-methylpentyl, 1,1-dimethylbutyl, 1,2-dimethylbutyl, 1,3-dimethylbutyl, 2,2-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethylpentyl, 2-ethylpentyl, 3-ethylpentyl, 1,1,2-trimethylbutyl, 1,1,3-trimethylbutyl, 1,2,2-trimethylbutyl, 2,2,3-trimethylbutyl, 1-ethyl-1-methylbutyl, 1-ethyl-2-methylbutyl, 1-ethyl-3-methylbutyl, 1-propylbutyl, 1-isopropylbutyl, octyl, 6-methylheptyl, nonyl, 7-methyloctyl, decyl, 8-methylnonyl. Thus, "$C_1$ to $C_{10}$ alkyl" means straight or branched carbon chain alkyl having 1 to 10 carbon atoms.

As the examples of "halogen", there are chlorine, bromine, iodine.

Some of the compounds of formula (I) can form salts including pharmaceutically acceptable salts or pharmacologically acceptable salts. Examples of such salts are salts of inorganic acids such as hydrochloric acid, hydrobromic acid, hydroiodic acid, sulfuric acid, nitric acid, phosphoric acid; and salts of organic acids such as formic acid, acetic acid, oxalic acid, citric acid, succinic acid, fumaric acid, maleic acid, tartaric acid, methanesulfonic acid, ethanesulfonic acid.

The compounds of this invention include compounds having asymmetric carbon atom(s) and hence optical isomers. This invention includes all of the isomers individually and in any mixture, such as racemic compound, optically active isomer, and diastereoisomer.

The compounds of this invention can be produced by various processes; typical production processes are explained hereinafter:

Process 1:

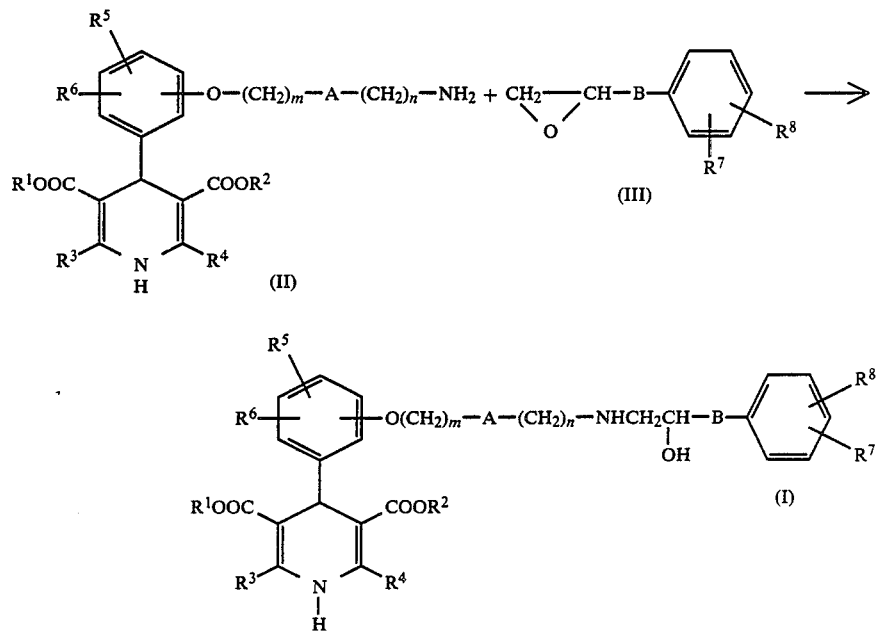

Compounds (I) can thus be produced by reacting dihydropyridine derivative (II) having an amino-substituted side chain as the substituent of phenyl at the 4-position of the dihydropyridine ring) with epoxy compound (III).

An equimolar or excess molar amount of either of the compounds(II) and (III) is used for the reaction, and the reaction is performed in the absence or presence of solvent which does not take part in the reaction. Examples of the solvent are organic solvents such as alcohol, (e.g. methanol, ethanol, isopropanol, etc.), ether (e.g. ethyl ether), tetrahydrofuran, ethyl acetate, dimethylformamide. The reaction can be performed at room temperature or under heating. The reaction time may vary according to other reaction conditions such as the solvent, etc.

Process 2:

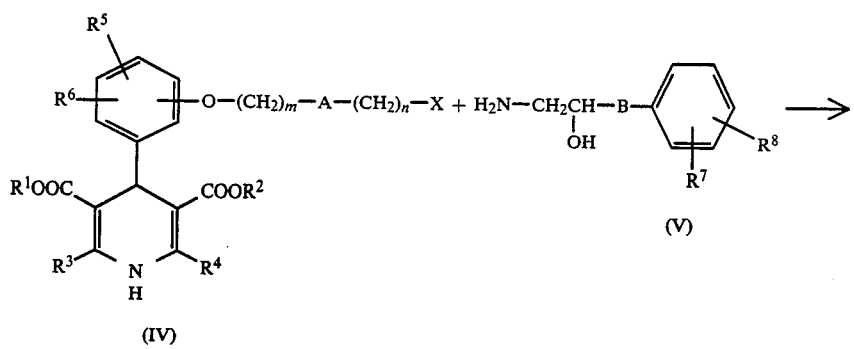

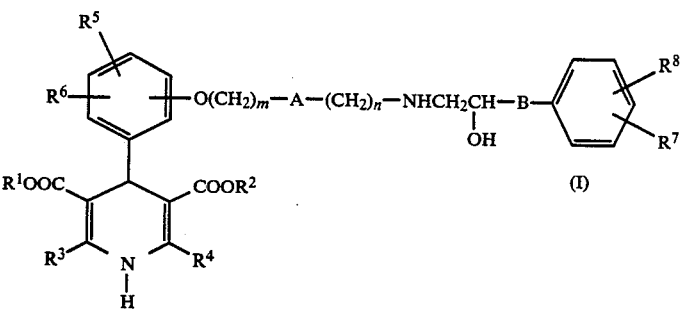

In the above formulae, X represents a halogen atom or an organic sulfonic acid radical, and hereinafter has the same significance.

Compounds (I) can thus be produced by reacting dihydropyridine derivative (IV) (having a halogeno-substituted or organic sulfonic acid radical-substituted side chain as the 4-phenyl substituent of of the dihydropyridine ring) with amine derivative (V).

Practical examples of "halogen" for X are chlorine, bromine, iodine; and of "organic sulfonic acid radical" for X are alkanesulfonic acid radical (alkylsulfonyloxy) such as methanesulfonic acid radical (methanesulfonyloxy), ethane sulfonic acid radical (ethanesulfonyloxy); and aromatic sulfonic acid radical such as toluenesulfonyl acid radical (toluenesulfonyloxy), benzenesulfonic acid radical (benzenesulfonyloxy).

When using dihydropyridine derivative having a halogeno-substituted side chain as the 4-phenyl substituent of the dihydropyridine ring, the reaction can be performed in the presence or absence of a solvent. Any solvents which do not take part in the reaction can be used. Examples of the solvent usually used are organic solvent such as benzene, toluene, xylene, dimethylformamide, dichloromethane, dichloroethane, methanol, and ethanol. It is preferred that the reaction be performed by reacting compound (IV) with an equimolar or excess molar amount of compound (V). The reaction is usually performed at room temperature or under heating, or under reflux.

It may be preferred for smooth reaction to operate in the presence of a base. Examples of such a base are organic bases such as pyridine, picoline, N,N-dimethylaniline, N-methylmorpholine, trimethylamine, triethylamine, dimethylamine (that is, secondary or tertiary amines); and inorganic bases such as sodium carbonate, or potassium hydrogencarbonate. In order to avoid side-reactions (dialkylation, etc.) which may occur, one may protect the amino group of the compound (V) and then react the amino-protected compound with the compound (IV), and release the protective group after the reaction, in order to provide the desired compound (I) selectively. Practical examples of the protective group for an amino group are toluenesulfonyl group, an acetyl group, a phenacylsulfonyl group, a trifluoromethanesulfonyl group, or a bis-benzenesulfonyl group. The releasing of the protective groups can be carried out by hydrolysis in conventional manner; the hydrolysis may be acid- or alkali-hydrolysis.

When using dihydropyridine derivative having an organic sulfonic acid radical-substituted side chain as the 4-phenyl substituent of the dihydropyridine ring, an equimolar or excess molar amount of compound (V) is preferably reacted with compound (IV), usually at room temperature or under cooling. The reaction is usually performed in (organic) solvent which does not take part in the reaction, and examples of the solvent are ether, methanol, ethanol, toluene, and tetrahydrofuran. The reaction time may vary according to the starting materials and solvent, and the reaction conditions such as the reaction temperature.

Process 3:

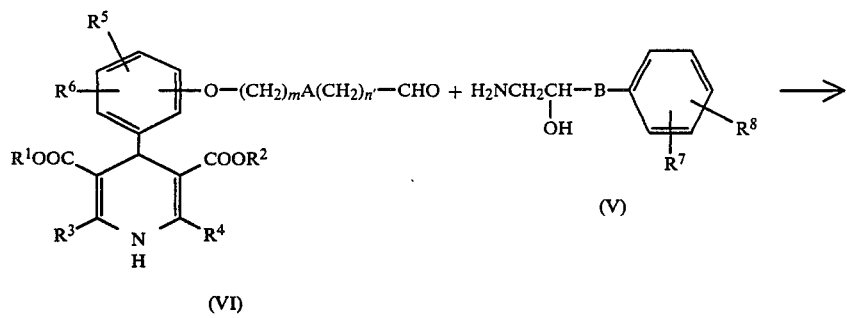

(VI)

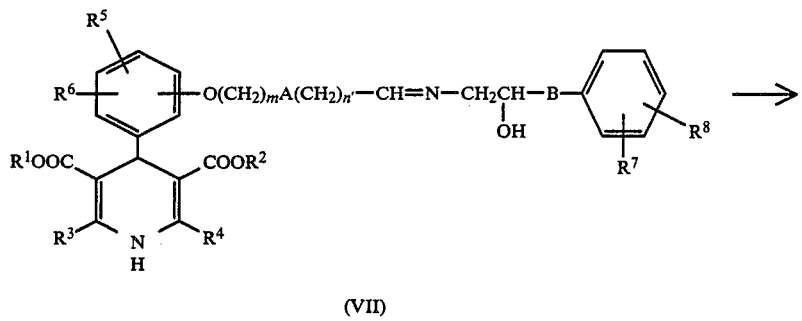

(VII)

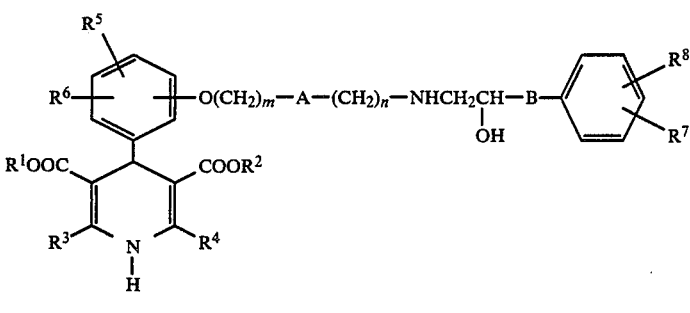

(I)

In the above formula, n' represents 0 or an integer of 1 to 4, and hereinafter has the same significance.

Compounds (I) can be prepared by reacting dihydropyridine derivative (VI) (which have a formyl-substituted side chain as the 4-phenyl substituent of the dihydropyridine ring) with amine derivative (V) to give a Schiff base (VII), and then reducing the Schiff base under conditions which do not reduce any nitro group in the compounds. The reaction to form the Schiff base can be performed in the presence or absence of a solvent. It is preferred to perform the reaction in a solvent. Any solvents which do not take part in the reaction can be used. Examples of the solvent used are organic solvent such as benzene, and alcohol such as methanol, or ethanol. The reaction is usually performed by reacting compound (VI) with an equimolar or excess molar amount of compound (V). The reaction is usually performed at room temperature or under heating, or under reflux. According to the kind of reaction, potassium hydroxide may be added in the reaction system, and/or it may be preferred to remove water formed in the course of the reaction by using a Dean-Stark trap.

In the step of reducing the Schiff base, a reducing agent may be added to the reaction solution containing the Schiff base formed (without isolating the Schiff base formed).

As reducing agents which do not reduce nitro group(s) and can selectively reduce the imino group in the Schiff base to give the desired compound (I), there are, for example, boron compounds such as sodium borohydride, lithium borohydride, and sodium borocyanohydride. The reduction can be performed in an organic solvent such as alcohol (for example, methanol, ethanol), acetic acid, or in water. The solvents may be used alone or in appropriate combination. The reaction is usually performed at room temperature or under heating. According to the kind of reaction, it may be preferred for smooth reaction to operate in the presence of a base in order to maintain the reaction system in a neutral or basic state. In such a case, e.g. methylamine, ethylamine, propylamine, dimethylamine, potassium hydroxyde, or sodium acetate may be added into the reaction system.

Process 4:

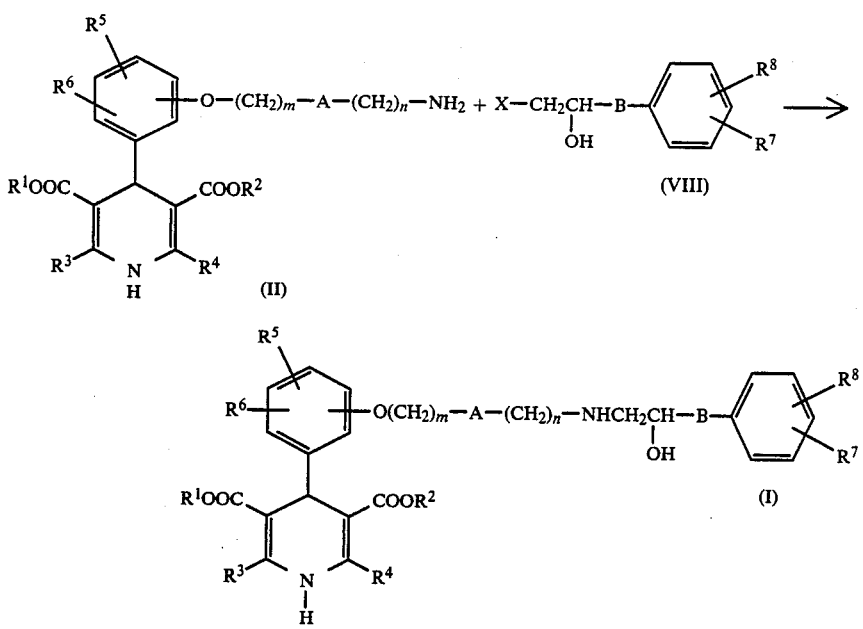

Compounds (I) can be produced by reacting compound (II) with compound (VIII) (halide compound or sulfonyloxy compound). The reaction conditions are almost the same as those of the before-mentioned Process 2.

Starting materials (II) may be produced by the method described in the Reference Examples of this application, or by other suitable reaction process. Among starting materials (IV), dihydropyridine compounds having organic sulfonyloxy can be produced by reacting organic sulfonyl halide with a dihydropyridine compound having a hydroxyl-substituted side chain at the 4-phenyl of the dihydropyridine ring; and dihydropyridine compounds having halogeno-substituted side chain can be produced by the method described in the Reference Examples of this application.

Starting materials (VI) can be produced by various methods. For example, a compound (IV) is reacted with Grignard reagent and ortho-formic acid ester, and then the formed compound is hydrolyzed to give the compound (VI).

A free form of the formula (I) compound or a salt of the compound (I) can be obtained after the above reactions. A salt of the formula (I) compound may be produced by performing a foregoing production process using a salt of the starting compound, or by applying a salt-forming reaction to the free formula (I) compound.

The formula (I) compounds and salts can be separated and purified in ordinary manner, such as extraction with organic solvent, crystallization, column chromatography. In the compounds of this invention, there are various isomers, e.g. racemic compounds, optically active isomers, diastereoisomers, alone or in combination. A single isomer can be obtained using a suitable starting material, or by a usual resolution method. By applying e.g. fractional recrystallization or chromatography to a diastereoisomer-mixture, each diastereoisomer can be separated.

The compounds of this invention of the formula (I) and their salts possess both $Ca^{2+}$-antagonistic and beta-adrenoceptor blocking activities. Furthermore, some compounds of this invention possess cardiac $beta_1$-adrenoceptor blocking activity, intrinsic sympathomimetic activity (ISA) or alpha-adrenoceptor blocking activity. Thus the compounds are useful for the treatment or prevention of ischemic heart diseases such as angina pectoris, myocardial infarction, and also for the treatment or prevention of cardiovascular disorders such as hypertension and cardiac arrythmia, apparently without side effects.

Compounds of this invention also possess cerebral vasodilating and central nervous system improving action and so may also be useful agents for inhibiting cerebral vasospasm and improving the central nervous system.

These pharmacological properties of compounds of this invention were evaluated in the following pharmacological experiments. Compounds of this invention lowered blood pressure and increased coronary blood flow after intravenous injection (effective dose range 0.01 to 3 mg/kg i.v.), dilated coronary artery after intracoronary injection (effective dose range 1 to 300 μg i.a.), produced beta-adrenoceptor blocking effect after intravenous injection (effective dose range 0.1 to 3 mg/kg i.v.) and also reduced cardiac work and myocardial oxygen consumption.

These pharmacological experiments also showed that the antihypertensive and coronary vasodilating activities of some compounds of this invention lasted longer than those of known dihydropyridine derivatives.

The pharmacological effects of compounds of this invention are shown in the following test methods and results.

METHODS (1) Hemodynamic effects

Mongrel dogs of either sex were anesthetized with pentobarbital sodium (30 mg/kg iv). The animals were artificially ventilated with room air. The chest was opened at the left 4th intercostal space. Mean arterial blood pressure (MBP), heart rate (HR), left ventricular pressure (LVP), max. dLVP/dt, mean pulmonary arterial blood pressure (MPAP), cardiac output (CO) and coronary blood flow (Cor. BF) were measured. The test compounds were injected into the femoral vein. Hemodynamic effects of these compounds were compared with that of well known $Ca^{2+}$-antagonists.

Table 1 (column 1) indicates the percent changes of MBP and Cor. BF from control values induced by intravenous injection of test compounds.

(2) Coronary vasodilating effects

Mongrel dogs of either sex were anesthetized and ventilated as previously described. A thoracotomy was performed at the 4th intercostal space. Following an intravenous injection of heprin (1000 units/kg), blood from the distal end of the cannulated carotid artery was pumped into circumflex branch of the left coronary artery using a servocontrolled peristaltic pump which maintained a constant perfusion pressure of 120 mmHg by means of a pump controller. An electromagnetic flow probe was inserted in the circuit to record blood flow through the cannulated coronary artery. The test compounds were administered directly into the rubber tubing connected close to the coronary artery cannula. Coronary vasodilating potency of the test compounds was by calculating the dose required to produce 100% increase of Cor. BF ($ED_{100}$ pap), when the maximum responses to papaverine at a dose of 300 μg ia was expressed at 100% response. Table 1 (column 2) shows $ED_{100}$ pap and the duration of action of coronary vasodilating effect of test compounds.

(3) Beta-adrenoceptor blocking effects

Beta-adrenoceptor blocking effect of test compounds was determined according to the method of Tachikawa and Takenaka (Pharmacological studies on 1-(7-indenyloxy)-3-isopropylaminopropan-2-ol hydrochloride (YB-2); Arch. Int. pharmacodyn., 202, 79–92, 1973) using male Wistar rats. The rats were pretreated with reserpine (8 mg/kg ip), 18 hr before experiments. The rats were anesthetized with pentobarbital sodium (55 mg/kg ip) and vagotomized bilaterally at the neck. The heart rate was measured with a cardiotachometer triggered by the QRS of the ECG (lead II) and recorded on a polygraph. After the control response to isoproterenol at a dose of 0.1 μg/kg iv was obtained, the test compound was injected iv in increasing doses at 20 min intervals. The mean dose producing 50% blockade of the positive chronotropic response to isoproterenol ($ED_{50}$) was estimated from dose-response curves obtained by plotting inhibition percentage against log cumulative dose of the test compound (Table 1, column 3).

In this series of experiments, intrinsic sympathomimetic activity (ISA) was also evaluated. The results are shown in Table 1 (column 4), wherein "−" represents that an increase in HR was scarcely observed, "+" represents an increase in HR of 10 to 19 beats/min, "++" represents an increase in HR of 20 to 29 beats/min, and "+++" represents an increase in HR of above 30 beats/min.

TABLE 1

Summary of pharmacological effects of test compounds

| | (1) | | | (2) | | (3) Beta Blocking | (4) |
|---|---|---|---|---|---|---|---|
| | M B P | | | | | | |
| Exp. No. | mg/kg iv | (%) | Cor. BF (%) | $ED_{100}$ pap μg ia | Duration min | $ED_{50}$ mg/kg iv | ISA |
| 1 | 0.1 | −7 | 21 | 75 | 15 | 0.13 | +++ |
|   | 0.3 | −17 | 69 | | | | |
| 8 | 1.0 | −29 | 10 | 645 | 60 | 0.31 | + |
| 10 | 0.3 | −12 | 26 | 400 | 60< | 0.73 | − |
| 12 | 0.3 | −18 | 14 | 475 | 60< | 2.58 | − |
| 15 | 1.0 | −33 | 96 | 228 | 60< | 0.70 | − |
| 16 | 1.0 | −31 | 97 | 162 | 60< | 0.39 | − |
| 17 | 1.0 | −35 | 94 | 158 | 60< | 3.53 | − |
| 18 | 0.3 | −13 | 20 | 285 | 60 | 3.11 | − |
| 23 | 1.0 | −32 | 64 | 780 | 60< | 0.03 | − |
| 24 | 1.0 | −33 | 62 | 245 | 60 | 1.50 | − |
| 26 | 1.0 | −38 | 43 | 600 | 40 | 0.53 | − |
| 28 | 1.0 | −28 | 70 | 555 | 30 | 0.27 | − |
| 34 | 0.3 | −18 | 3 | 175 | 60< | 0.90 | − |
| 42 | 1.0 | −13 | 8 | 515 | 60< | 0.50 | − |
| Diltiazem | 0.3 | −30 | 90 | 51 | 20 | NT | |
| Propranolol | | NT | | NT | | 0.063 | − |

NT = Not tested

Medicaments containing a compound or compounds according to the invention may be prepared by conventional methods using conventional carriers or excipients. Medicaments may contain one kind of the compound or many kinds of the compound of this invention. The compounds may be in free or salt form. They may for example be administered orally as tablets, troches, pills, capsules, granules; parenterally by intravenous or intramuscular injection; as suppositories; or in other suitable administration forms in the liquid, fluid, or solid state, e.g. as ointment adhesive tape or plaster. Conventional carriers or excipients used for the medicaments are non-toxic solid or liquid pharmaceutical materials, and examples thereof are lactose, magnesium stearate, starch, talc, gelatine, agar, pectine, arabia gum, olive oil, sesame oil, cacao butter, ethylene glycol.

The appropriate dose is determined in each case considering factors such as the symptom, age and sex of the patient. For an adult a daily total of 1–200 mg is usually administered by intravenous injection in one to several doses.

The invention is further illustrated by the following Reference Examples and Examples. In the following Reference Examples and Examples, mp. Anal, Cal, Fnd, and NMR are abbreviations for melting point, elementary analysis values, calculated, found, and nuclear magnetic resonance spectrum.

REFERENCE EXAMPLE 1

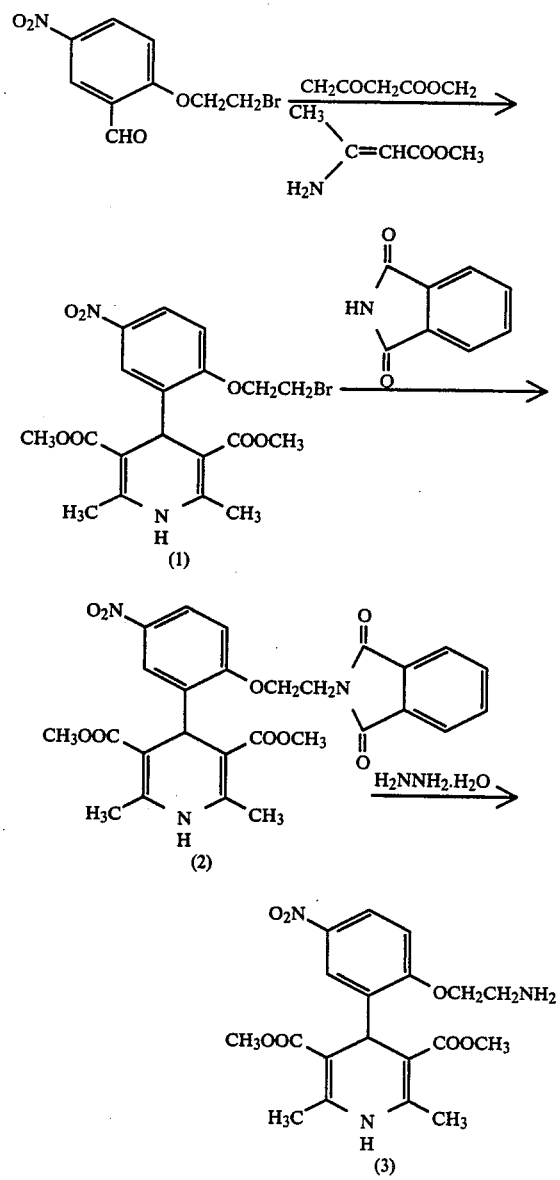

(1) In isopropanol were dissolved 23 g of 2-(2-bromoethoxy)-5-nitrobenzaldehyde, 11.5 g of 3-aminocrotonic acid methyl ester and 11.6 g of methyl acetoacetate, and the mixture was refluxed under heating for 7 hours. The reaction solution was cooled, and precipitated crystals were collected by filtration. The crystals were washed with methanol, and air-dried to give 33 g of crude crystals of dimethyl 4-[(2-bromoethoxy)-5-nitrophenyl]-2,6-dimethyl-1,4-dihydropyridine-3,5-dicarboxylate. The product was directly used for the next process without purification.

(2) In 25 ml of N,N-dimethylformamide were suspended 17 g of dimethyl 4-[(2-bromoethoxy)-5-nitrophenyl]-2,6-dimethyl-1,4-dihydropyridine-3,5-dicarboxylate and 7.4 g potassium phthalimide, and the suspension was heated at 120°-130° C. for 3 hours. The reaction mixture was poured into 750 ml of ice-water, and precipitated crystals were collected by filtration. The crystals were washed with water and air-dried to give 19.6 g of crude crystals of dimethyl 4-[(2-phthalimidoethoxy)-5-nitrophenyl]-2,6-dimethyl-1,4-dihyropyridine-3,5-dicarboxylate.

(3) A solution of 12 g of dimethyl 4-[(2-phthalimidoethoxy)-5-nitrophenyl]-2,6-dimethyl-1,4-dihydropyridine-3,5-dicarboxylate and 6 ml of hydrazine hydrate in 240 ml of ethanol was refluxed under heating for 30 minutes. Precipitated crystals were filtered off while hot, and the filtrate was concentrated under reduced pressure to remove the solvent. After adding water to the residue, the product was extracted with ethyl acetate. The extract was washed with water, and dried over anhydrous sodium sulfate, and the solvent was distilled off under reduced pressure. Crude crystals thus obtained were recrystallized from methanol to give 6 g of dimethyl 4-[2-(2-aminoethoxy)-5-nitrophenoxy]-2,6-dimethyl-1,4-dihydropyridine-3,5-dicarboxylate.

mp. 228°~230° C.

|  | Anal ($C_{19}H_{22}N_2O_7$) | | |
|---|---|---|---|
|  | C (%) | H (%) | N (%) |
| Cal | 56.29 | 5.72 | 10.36 |
| Fnd | 56.06 | 5.82 | 10.10 |

NMR (DMSO-$d_6$). δ(ppm); 2.24 (6H, s), 2.94 (2H, t), 3.48 (6H, s), 4.06 (2H, t), 5.24 (1H, s).

REFERENCE EXAMPLE 2

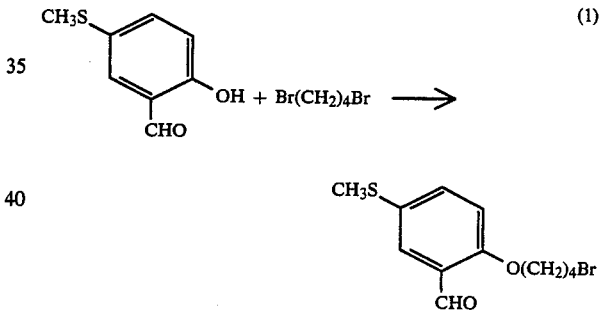

A solution of 18.3 g of 5-methylthiosalicylaldehyde, 235 g of 1,4-dibromobutane and 1.1 g of tetra-n-butylammonium hydrogen sulfate in 18 ml of water was heated at 70°-80° C. While stirring, 13.1 g of sodium hydroxide in 109 ml of water were added dropwise over a period of 4 hours, and then the formed mixture was heated for 2 hours. The mixture was cooled, and extracted with chloroform. The extract (organic layer separated) was washed with water, dried over anhydrous magnesium sulfate, and concentrated under reduced pressure to give 32.2 g of a crude product of 2-(4-bromobutoxy)-5-methylthiobenzaldehyde. This crude product was used directly for the next process without purification.

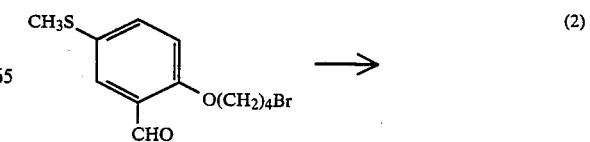

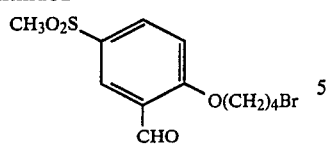

In 55 ml of dichloromethane was dissolved 10.9 g of 2-(4-bromobutoxy)-5-methylthiobenzaldehyde, and the solution was cooled to 0° C. A solution of 15.2 g of m-chloroperbenzoic acid in 165 ml of dichloromethane was added dropwise to the before-mentioned dichloromethane solution over a period of three hours. After 4 hours, saturated aqueous sodium hydrogen carbonate was added to the reaction mixture to neutralize it, and the mixture was extracted with chloroform. The extract (organic layer separated) was washed with saturated aqueous sodium hydrogen carbonate and water, dried over anhydrous magnesium sulfate, and concentrated under reduced pressure to give a crude product. The crude product was recrystallized from chloroform-ether to give 7.8 g of 2-(4-bromobutoxy)-5-methylsulfonylbenzaldehyde
mp. 103°–105° C.

(3)

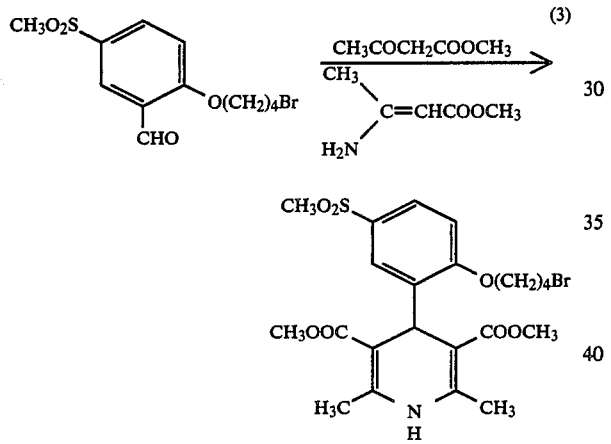

7.6 g of 2-(4-bromobutoxy)-5-methylsulfonylbenzaldehyde, 2.6 g of methyl acetoacetate and 2.9 g of 3-aminocrotonic acid methyl ester were dissolved in 16 ml of isopropanol, and the solution was heated for 5 hours. After cooling, precipitated crystals were collected by filtration, and recrystallized from methanol to give 6.3 g of dimethyl 4-[2(4-bromobutoxy)-5-methylsulfonylphenyl]-2,6-dimethyl-1,4-dihydropyridine-3,5-dicarboxylate.
mp. 191°–201° C.

(4)

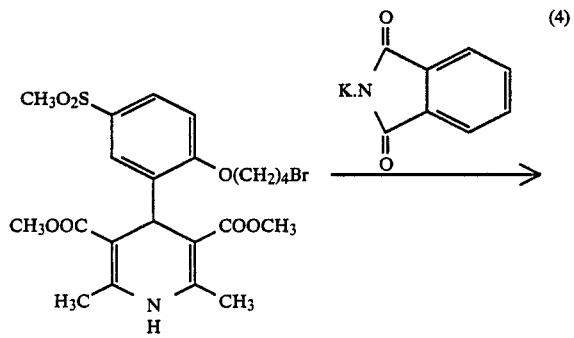

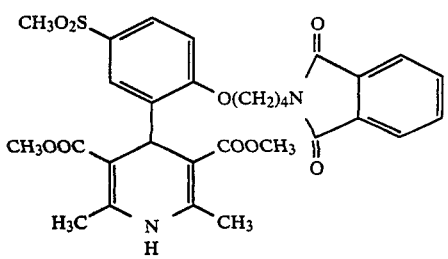

In 8 ml of N,N-dimethylformamide were suspended 6.3 g of dimethyl 4-[2-(4-bromobutoxy)-5-methylsulfonylphenyl]-2,6-dimethyl-1,4-dihydropyridine-3,5-dicarboxylate and 2.2 g of potassium phthalimide, and the suspension was heated for 1 hour at 120°–130° C. The reaction mixture was poured into ice-water, and precipitated solid materials were collected by filtration to give 7.0 g of a crude product of 4-[2-(4-phthalimidobutoxy)-5-methylsulfonylphenyl]-2,6-dimethyl-1,4-dihydropyridine-3,5-dicarboxylate. This product was used for the next process without purification.

(5)

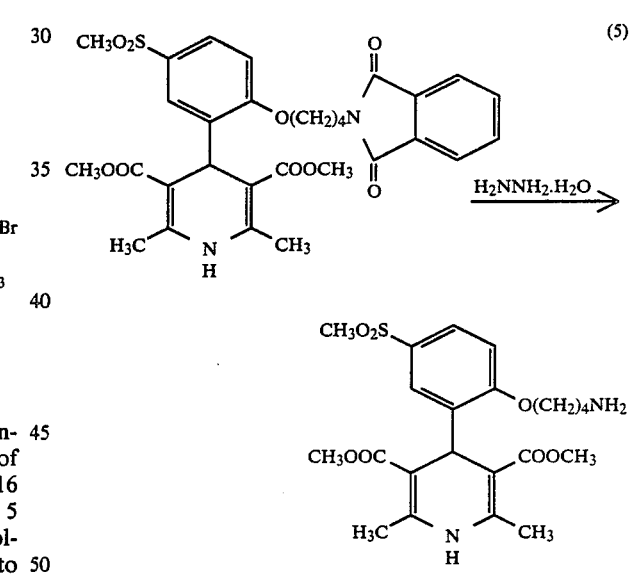

A solution of 6.9 g of dimethyl 4-[2-(4-phthalimidobutoxy)-5-methylsulfonylphenyl]-2,6-dimethyl-1,4-dihydropyridine-3,5-dicarboxylate and 5.9 g of hydrazine monohydrate in 170 ml of % ethanol(water: 5%) was refluxed under heating for 6 hours. After cooling, the reaction solution was concentrated under reduced pressure. The residue was extracted with chloroform, and the extract was washed with water, dried over anhydrous magnesium sulfate, and concentrated under reduced pressure. Crude crystals thus obtained were recrystallized from chloroform-ether to give 2.6 g of dimethyl 4-[2-(4-aminobutoxy)-5-methylsulfonylphenyl]-2,6-dimethyl-1,4-dihydropyridine-3,5-dicarboxylate.
mp. 184°–186° C.

REFERENCE EXAMPLE 3

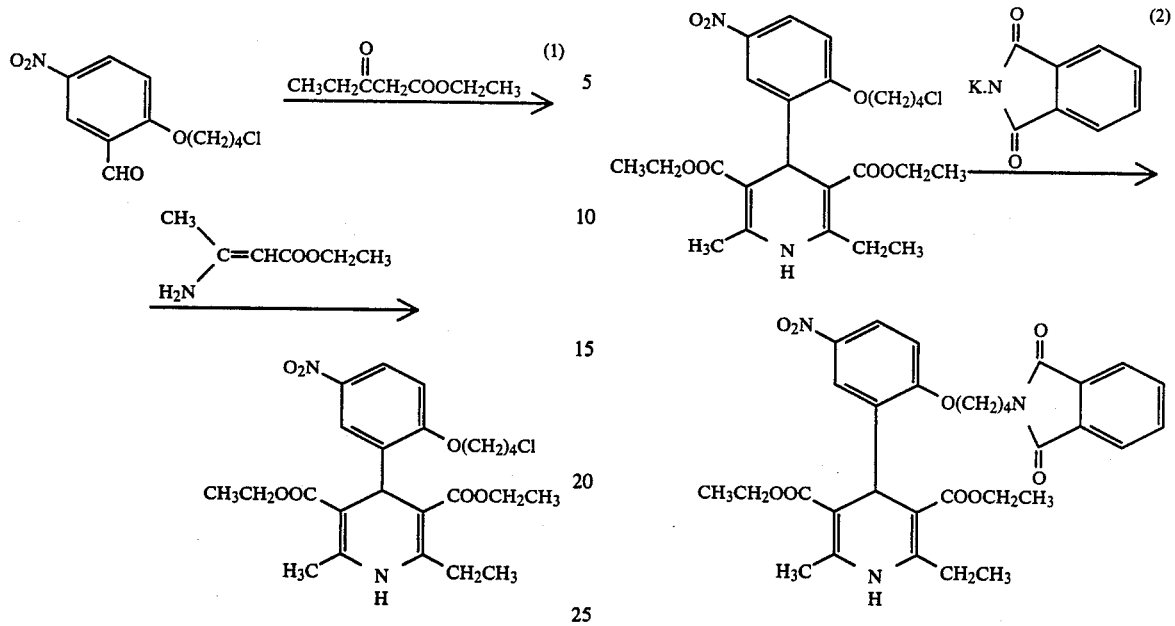

In 106 ml of dry benzene were dissolved 13.0 g of 2-(4-chlorobutoxy)-5-nitrobenzaldehyde, 7.28 g of ethyl propionylacetate, 0.20 ml of piperidine and 0.62 ml of acetic acid, and the solution was refluxed for 9 hours while removing water using a Dean-Stark trap. After cooling the reaction solution, 6.52 g of ethyl 3-aminocrotonate was added to the solution, and the mixture was refluxed under heating for 11 hours. After cooling the mixture, precipitated crude crystals were collected by filtration, and recrystallized from methanol to give 13.13 g of diethyl 2-ethyl-4-[2-(4-chlorobutoxy)-5-nitrophenyl]-6-methyl-1,4-dihydropyridine-3,5-dicarboxylate.
mp. 147°–149° C.

In 8 ml of N,N-dimethylformamide were suspended 10.26 g of diethyl 2-ethyl-4-[2-(4-chlorobutoxy)-5-nitrophenyl]-6-methyl-1,4-dihydropyridine-3,5-dicarboxylate and 3.84 g of potassium phthalimide, and the suspension was heated for 1 hour at 120°–130° C. The reaction mixture was poured into ice-water, and precipitated solid materials were collected by filtration to give 12.5 g of a crude product of diethyl 2-ethyl-4-[2-(4-phthalimidobutoxy)-5-nitrophenyl]-6-methyl-1,4-dihydropyridine-3,5-dicarboxylate. This product was used for the next process without purification.

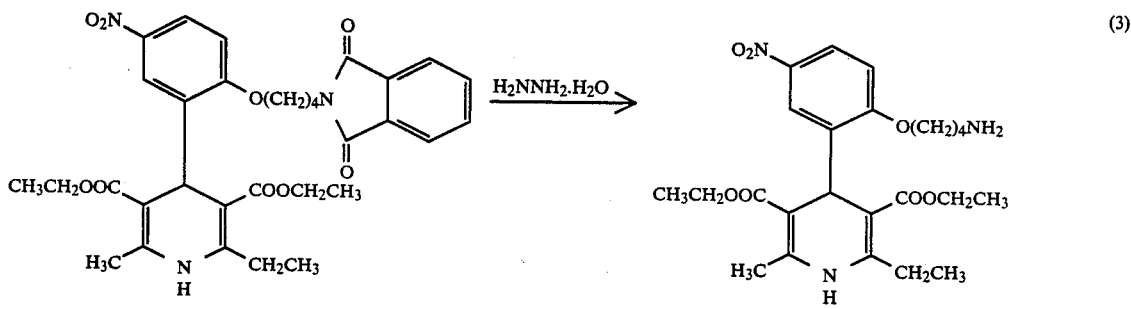

A solution of 12.4 g of diethyl 2-ethyl-4-[2-(4-phthalimidobutoxy)-5-nitrophenyl]-6-methyl-1,4-dihydropyridine-3,5-dicarboxylate and 10.4 g of hydrazine monohydrate in 270 ml of 95% ethanol (water: 5%) was refluxed under heating for 10 hours. After cooling the reaction solution, the solution was concentrated under reduced pressure, and the residue was extracted with chloroform. The extract was washed with water, dried over anhydrous magnesium sulfate, and concentrated under reduced pressure. Crude crystals thus obtained were recrystallized from chloroform-ether to give 6.4 g of diethyl 4-[2-(4-aminobutoxy)-5-nitrophenyl]-2-ethyl-6-methyl-1,4-dihydropyridine-3,5-dicarboxylate.
mp. 173.5°–175.5° C.

EXAMPLE 1

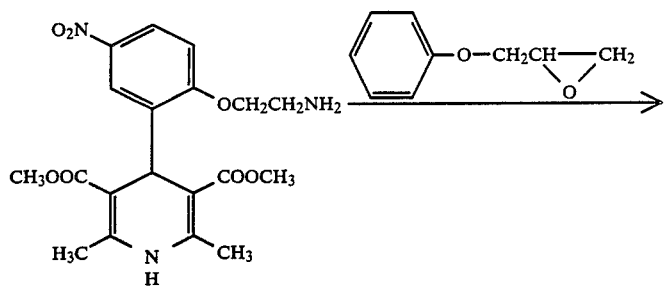

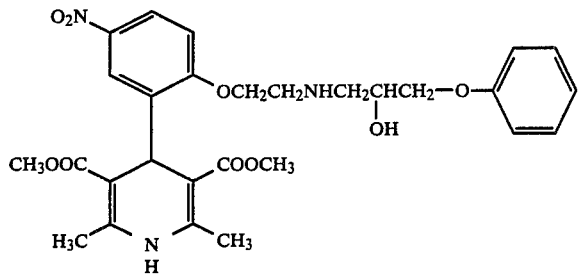

EXAMPLE 2

4 g of dimethyl 4-[2-(2-aminoethoxy)-5-nitrophenyl]-2,6-dimethyl-1,4-dihydropyridine-3,5-dicarboxylate (obtained in Reference Example 1) and 1.5 g of glycidyl phenyl ether were dissolved in 200 ml of methanol, and the mixture was allowed to stand for 2 days at room temperature. The reaction mixture was concentrated, and the residue was subjected to column chromatography on silica gel. The product was eluted with chloroform-methanol (98:2 v/v). Crude crystals were recrystallized from ethanol to give 1.8 g of dimethyl 4-[2-[2-(2-hydroxy-3-phenoxypropylamino)ethoxy]-5-nitrophenyl]-2,6-dimethyl-1,4-dihydropyridine-3,5-dicarboxylate.

mp. 189°–190° C.

| | Anal ($C_{28}H_{33}N_3O_9$) | | |
|---|---|---|---|
| | C (%) | H (%) | N (%) |
| Cal | 60.53 | 5.99 | 7.56 |
| Fnd | 60.43 | 6.05 | 7.42 |

NMR (DMSO-$d_6$). δ(ppm); 2.22 (6H, s), 3.47 (6H, s), 5.21 (1H, s).

EXAMPLES 2–13

By following the same procedure as in Example 1, the following compounds were obtained.

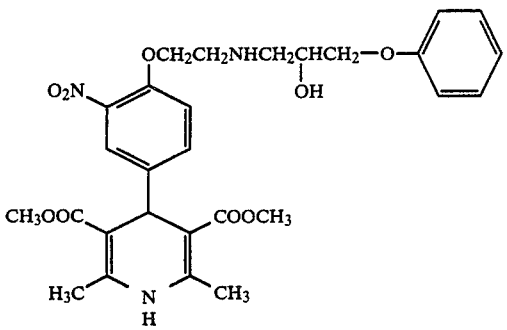

dimethyl 4-[4-[2-(2-hydroxy-3-phenoxypropylamino)ethoxy]-3-nitrophenyl]-2,6-dimethyl-1,4-dihydropyridine-3,5-dicarboxylate mp. 147°~149° C.

| | Anal ($C_{28}H_{33}N_3O_9$) | | |
|---|---|---|---|
| | C (%) | H (%) | N (%) |
| Cal | 60.53 | 5.99 | 7.56 |
| Fnd | 60.47 | 6.02 | 7.51 |

NMR (CDCl$_3$). δ(ppm); 2.35 (6H, s), 3.68 (6H, s), 4.26 (2H, t), 5.01 (1H, s).

EXAMPLE 3

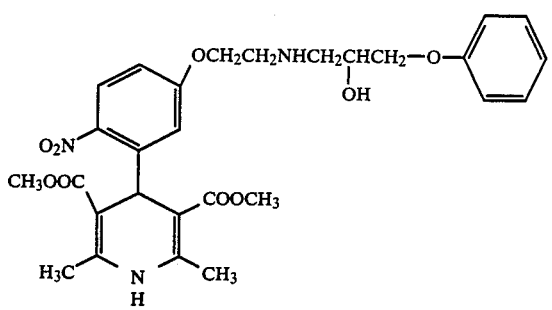

dimethyl
4-[5-[2-(2-hydroxy-3-phenoxypropylamino)ethoxy]-2-nitrophenyl]-2,6-dimethyl-1,4-dihydropyridine-3,5-dicarboxylate amorphous powder

|  | Anal ($C_{28}H_{33}N_3O_9$) | | |
|---|---|---|---|
|  | C (%) | H (%) | N (%) |
| Cal | 60.53 | 5.99 | 7.56 |
| Fnd | 60.41 | 6.06 | 7.41 |

NMR ($CDCl_3$).
$\delta$(ppm); 2.32 (6H, s), 3.58 (6H, s), 5.86 (1H, s).

EXAMPLE 4

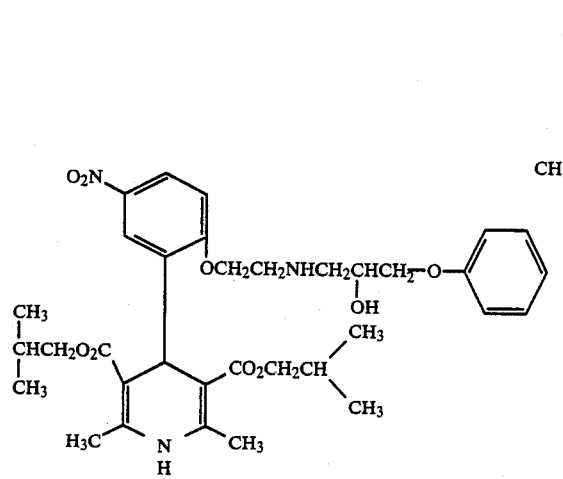

diisobutyl
4-[2-[2-(2-hydroxy-3-phenoxypropylamino)ethoxy]-5-nitrophenyl]-2,6-dimethyl-1,4-dihydropyridine-3,5-dicarboxylate mp. 165°~166° C.

|  | Anal ($C_{34}H_{45}N_3O_9$) | | |
|---|---|---|---|
|  | C (%) | H (%) | N (%) |
| Cal | 63.83 | 7.09 | 6.57 |
| Fnd | 63.55 | 7.13 | 6.49 |

NMR ($CDCl_3$) $\delta$(ppm); 0.84 (12H, dd), 1.86 (2H, m), 2.32 (6H, s), 3.78 (4H, d), 5.40 (1H, s).

EXAMPLE 5

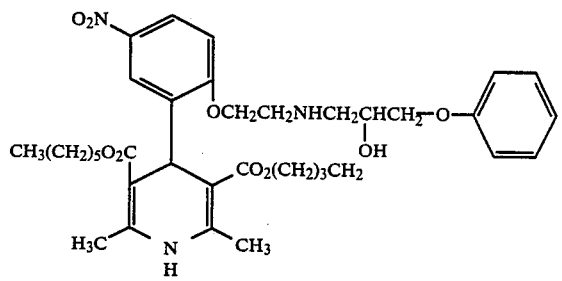

dihexyl
4-[2-[2-(2-hydroxy-3-phenoxypropylamino)ethoxy]-5-nitrophenyl]-2,6-dimethyl-1,4-dihydropyridine-3,5-dicarboxylate mp. 89°~90° C.

|  | Anal ($C_{38}H_{53}N_3O_9$) | | |
|---|---|---|---|
|  | C (%) | H (%) | N (%) |
| Cal | 65.59 | 7.68 | 6.04 |
| Fnd | 65.35 | 7.78 | 5.99 |

NMR ($CDCl_3$). $\delta$(ppm); 0.84 (6H, t), 2.30 (6H, s), 5.36 (1H, s).

EXAMPLE 6

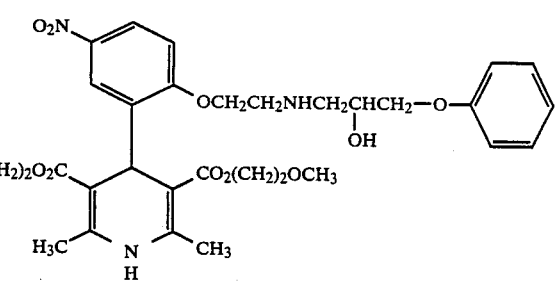

bis(2-methoxyethyl)
4-[2-[2-(2-hydroxy-3-phenoxypropylamino)ethoxy]-5-nitrophenyl]-2,6-dimethyl-1,4-dihydropyridine-3,5-dicarboxylate mp. 109°~110° C.

|  | Anal ($C_{32}H_{41}N_3O_{11}$) | | |
|---|---|---|---|
|  | C (%) | H (%) | N (%) |
| Cal | 59.71 | 6.42 | 6.53 |
| Fnd | 59.57 | 6.36 | 6.44 |

NMR (CDCl₃). δ(ppm): 2.28 (6H, s), 2.6~3.2 (4H, m), 3.28 (6H, s), 3.48 (4H, t), 5.36 (1H, s).

EXAMPLE 7

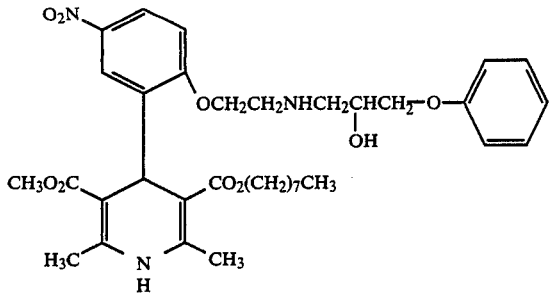

methyl octyl 4-[2-[2-(2-hydroxy-3-phenoxypropylamino)ethoxy]-5-nitrophenyl]-2,6-dimethyl-1,4-dihydropyridine-3,5-dicarboxylate Amorphous powder

|  | Anal (C₃₅H₄₇N₃O₉) | | |
|---|---|---|---|
|  | C (%) | H (%) | N (%) |
| Cal | 64.30 | 7.25 | 6.43 |
| Fnd | 64.23 | 7.46 | 6.48 |

NMR (CDCl₃). δ(ppm); 0.88 (3H, t), 2.32 (6H, s), 3.64 (3H, s), 5.40 (1H, s).

EXAMPLE 8

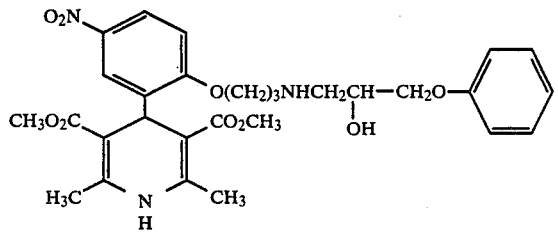

dimethyl 4-[2-[3-(2-hydroxy-3-phenoxypropylamino)propoxy]-5-nitrophenyl]-2,6-dimethyl-1,4-dihydropyridine-3,5-dicarboxylate amorphous powder

|  | Anal (C₂₉H₃₅N₃O₉) | | |
|---|---|---|---|
|  | C (%) | H (%) | N (%) |
| Cal | 61.15 | 6.19 | 7.38 |
| Fnd | 60.91 | 6.48 | 7.10 |

NMR (CDCl₃). δ(ppm); 2.0~2.20 (2H, m), 2.30 (6H, s), 2.8~3.0 (4H, m), 3.60 (6H, s), 4.0~4.20 (4H, m), 5.32 (1H, s).

EXAMPLE 9

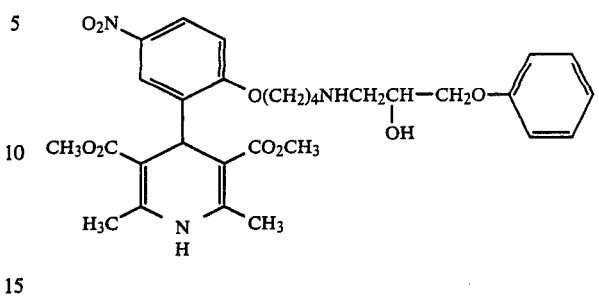

dimethyl 4-[2-[4-(2-hydroxy-3-phenoxypropylamino)butoxy]-5-nitrophenyl]-2,6-dimethyl-1,4-dihydropyridine-3,5-dicarboxylate amorphous powder

|  | Anal (C₃₀H₃₇N₃O₉) | | |
|---|---|---|---|
|  | C (%) | H (%) | N (%) |
| Cal | 61.74 | 6.39 | 7.20 |
| Fnd | 61.66 | 6.51 | 7.17 |

NMR (CDCl₃). δ(ppm); 1.60~2.0 (4H, m), 2.28 (6H, s), 2.70~2.90 (4H, m), 3.56 (6H, s), 3.92~4.16 (4H, m), 5.32 (1H, s).

EXAMPLE 10

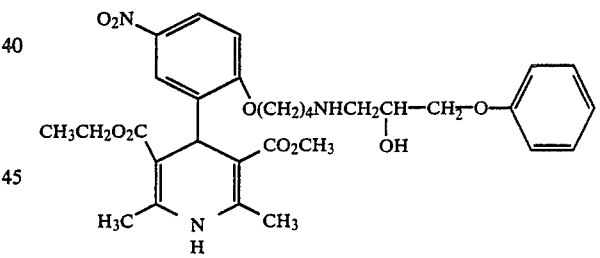

ethyl methyl 4-[2-[4-(2-hydroxy-3-phenoxypropylamino)butoxy]-5-nitrophenyl]-2,6-dimethyl-1,4-dihydropyridine-3,5-dicarboxylate amorphous powder

|  | Anal (C₃₁H₃₉N₃O₉) | | |
|---|---|---|---|
|  | C (%) | H (%) | N (%) |
| Cal | 62.30 | 6.58 | 7.03 |
| Fnd | 62.38 | 6.77 | 6.95 |

NMR (CDCl₃). δ(ppm); 1.16 (3H, t), 1.60~1.90 (4H, m), 2.30 (6H, s), 2.60~2.90 (4H, m), 3.94 (3H, s), 3.80~4.20 (6H, m), 5.28 (1H, s).

EXAMPLE 11

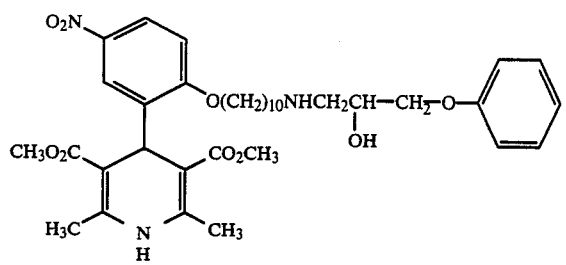

dimethyl
4-[2-[10-(2-hydroxy-3-phenoxypropylamino)decyloxy]-5-nitrophenyl]-2,6-dimethyl-1,4-dihydropyridine-3,5-dicarboxylate amorphous powder

| | Anal ($C_{30}H_{49}N_3O_9$) | | |
|---|---|---|---|
| | C (%) | H (%) | N (%) |
| Cal | 64.75 | 7.40 | 6.29 |
| Fnd | 64.27 | 7.65 | 6.25 |

NMR (CDCl$_3$). δ(ppm); 1.20~1.60 (16H, m), 2.30 (6H, s), 2.50~2.90 (4H, m), 3.56 (6H, s), 3.96~4.10 (4H, m), 5.34 (1H, s).

EXAMPLE 12

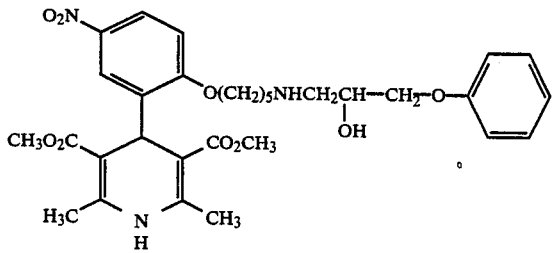

dimethyl
4-[2-[5-(2-hydroxy-3-phenoxypropylamino)pentyloxy]-5-nitrophenyl]-2,6-dimethyl-1,4-dihydropyridine-3,5-dicarboxylate amorphous powder

| | Anal ($C_{31}H_{39}N_3O_9$) | | |
|---|---|---|---|
| | C (%) | H (%) | N (%) |
| Cal | 62.30 | 6.58 | 7.03 |
| Fnd | 62.43 | 6.87 | 7.18 |

NMR (CDCl$_3$). δ(ppm); 1.40~1.90 (6H, m), 2.30 (6H, s), 2.60~2.90 (4H, m), 3.56 (6H, s), 3.90~4.20 (4H, m), 5.30 (1H, s).

EXAMPLE 13

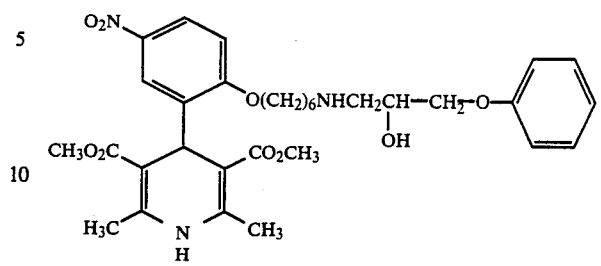

dimethyl
4-[2-[6-(2-hydroxy-3-phenoxypropylamino)hexyloxy]-5-nitrophenyl]-2,6-dimethyl-1,4-dihydropyridine-3,5-dicarboxylate amorphous powder

| | Anal ($C_{32}H_{41}N_3O_9$) | | |
|---|---|---|---|
| | C (%) | H (%) | N (%) |
| Cal | 62.83 | 6.76 | 6.87 |
| Fnd | 62.58 | 6.83 | 6.88 |

NMR (CDCl$_3$). δ(ppm); 1.40~1.60 (8H, m), 2.30 (6H, s), 2.60~2.90 (4H, m), 3.60 (6H, s), 3.90~4.10 (4H, m), 5.32 (1H, s).

EXAMPLE 14

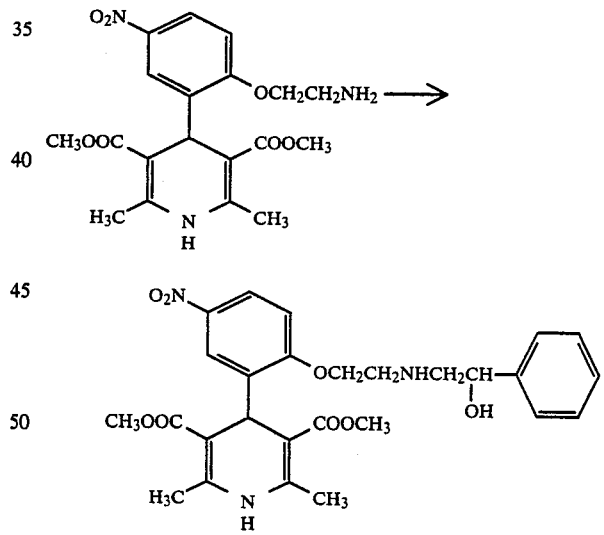

In 30 ml of N,N-dimethylformamide were dissolved 2 g of dimethyl 4-[2-(2-aminoethoxy)-5-nitrophenyl]-2,6-dimethyl-1,4-dihydropyridine-3,5-dicarboxylate and 0.6 g of styrene oxide, and the solution thus formed was allowed to stand for 2 days at room temperature. The reaction solution was concentrated under reduced pressure, and the residue was subjected to silica gel column chromatography. The product was eluted with chloroform-methanol (95:5 v/v). Crude crystals were recrystallized from ethyl acetate to give 500 mg of dimethyl 4-[2-[2-(β-hydroxyphenethylamino)ethoxy]-5-nitrophenyl]-2,6-dimethyl-1,4-dihydropyridine-3,5-dicarboxylate.

mp. 135°–137° C.

| Anal (C27H31N3O8) | | | |
|---|---|---|---|
| | C (%) | H (%) | N (%) |
| Cal | 61.71 | 5.95 | 8.00 |
| Fnd | 61.88 | 5.84 | 7.94 |

NMR (DMSO-d6). δ(ppm): 1.34 (3H, s), 3.58 (3H, s), 4.20 (2H, t), 4.82 (1H, t), 5.36 (1H, s).

EXAMPLE 15

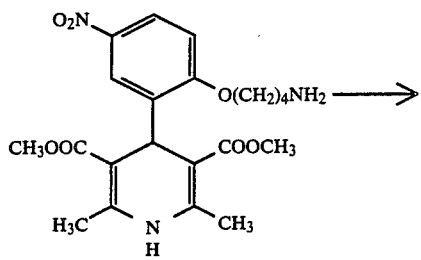

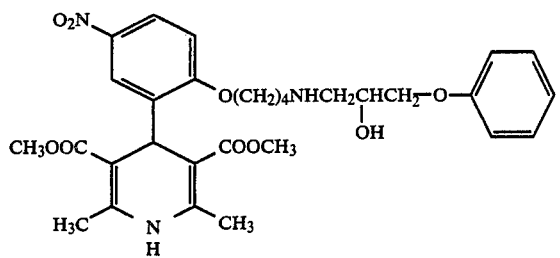

In 1,300 ml of methanol were dissolved 13 g of dimethyl 4-[2-(4-aminobutoxy)-5-nitrophenyl]-2,6-dimethyl-1,4-dihydropyridine-3,5-dicarboxylate and 4.5 g of glycidyl phenyl ether, and the solution thus formed was refluxed under heating for 16 hours. The solvent was distilled off under reduced pressure. The residue was subjected to silica gel column chromatography, and the product was eluted with chloroform-methanol (96:4 v/v). Crude crystals were recrystallized from ethanol to give 9 g of dimethyl 4-[2-[4-(2-hydroxy-3-phenoxypropylamino)butoxy]-5-nitrophenyl]-2,6-dimethyl-1,4-dihydropyridine-3,5-dicarboxylate.

mp. 131°–133° C.

| Anal (C30H37N3O9) | | | |
|---|---|---|---|
| | C (%) | H (%) | N (%) |
| Cal | 61.74 | 6.39 | 7.20 |
| Fnd | 61.61 | 6.49 | 7.21 |

NMR (CDCl3). δ: (ppm); 1.6–2.0 (4H, m), 2.28 (6H, s), 2.7–2.9 (4H, m), 3.56 (6H, s), 3.9–4.2 (5H, m), 5.30 (1H, s), 6.6–7.1 (3H, m), 7.1–7.4 (3H, m), 7.9–8.2 (2H, m).

This product was treated with an ethanolic solution of hydrogen chloride to give the hydrochloric acid salt thereof, which was recrystallized from ethanol to provide dimethyl 4-[2-[4-(2-hydroxy-3-phenoxypropylamino)butoxy]-5-nitrophenyl]-2,6-dimethyl-1,4-dihydropyridine-3,5-dicarboxylate hydrochloride.

mp. 117°–120° C.

| Anal (C30H37N3O9.HCl.H2O) | | | | |
|---|---|---|---|---|
| | C (%) | H (%) | N (%) | Cl (%) |
| Cal | 56.47 | 6.32 | 6.59 | 5.56 |
| Fnd | 56.68 | 6.38 | 6.32 | 5.53 |

EXAMPLE 16

(a) By following the same procedure as in Example 15 using (S)-glycidyl phenyl ether, (S)-(−)-dimethyl 4-[2-[4-(2-hydroxy-3-phenoxypropylamino)butoxy]-5-nitrophenyl]-2,6-dimethyl-1,4-dihydropyridine-3,5-dicarboxylate was obtained.

mp. 144°–146° C.

$[\alpha]_D^{24}$ −2.1° (C=1.08, MeOH)

| Anal (C30H37N3O9) | | | |
|---|---|---|---|
| | C (%) | H (%) | N (%) |
| Cal | 61.74 | 6.39 | 7.20 |
| Fnd | 61.57 | 6.55 | 7.21 |

(b) The product obtained at 16(a) above was treated with an ethanol solution of hydrogen chloride to give the hydrochloric acid salt thereof, which was recrystallized from ethanol to provide pure (s)-(−)-dimethyl 4-[2-[4-(2-hydroxy-3-phenoxypropylamino)butoxy]-5-nitrophenyl]-2,6-dimethyl-1,4-dihydropyridine-3,5-dicarboxylate hydrochloride.

mp. 187°–189° C.

$[\alpha]_D^{24}$ −12.5° (c=1.04, MeOH)

| Anal (C30H37N3O9.HCl) | | | |
|---|---|---|---|
| | C (%) | H (%) | N (%) |
| Cal | 58.11 | 6.18 | 6.78 |
| Fnd | 58.00 | 6.31 | 6.71 |

EXAMPLE 17

(a) By following the same procedure as in Example 16 using (R)-glycidyl phenyl ether, (R)-(+)-dimethyl 4-[2-[4-(2-hydroxy-3-phenoxypropylamino)butoxy]-5-nitrophenyl]-2,6-dimethyl-1,4-dihydropyridine-3,5-dicarboxylate was obtained.

mp. 144°–146° C.

$[\alpha]_D^{24}$ +2.2° (c=1.07, MeOH)

| Anal (C30H37N3O9) | | | |
|---|---|---|---|
| | C (%) | H (%) | N (%) |
| Cal | 61.74 | 6.39 | 7.20 |
| Fnd | 61.58 | 6.56 | 7.17 |

(b) The product obtained at 17(a) above was treated with an ethanol solution of hydrochloric acid to give the hydrochloric acid salt thereof, which was recrystallized from ethanol to give pure (R)-(+)-dimethyl 4-[2-[4-(2-hydroxy-3-phenoxypropylamino)butoxy]-5-nitrophenyl]-2,6-dimethyl-1,4-dihydropyridine-3,5-dicarboxylate hydrochloride.

mp. 191°–193° C.

$[\alpha]_D^{24}$ +12.1° (c=1.01, MeOH)

| Anal (C30H37N3O9.HCl) | | | |
|---|---|---|---|
| | C (%) | H (%) | N (%) |
| Cal | 58.11 | 6.18 | 6.75 |
| Fnd | 58.04 | 6.29 | 6.67 |

EXAMPLE 18

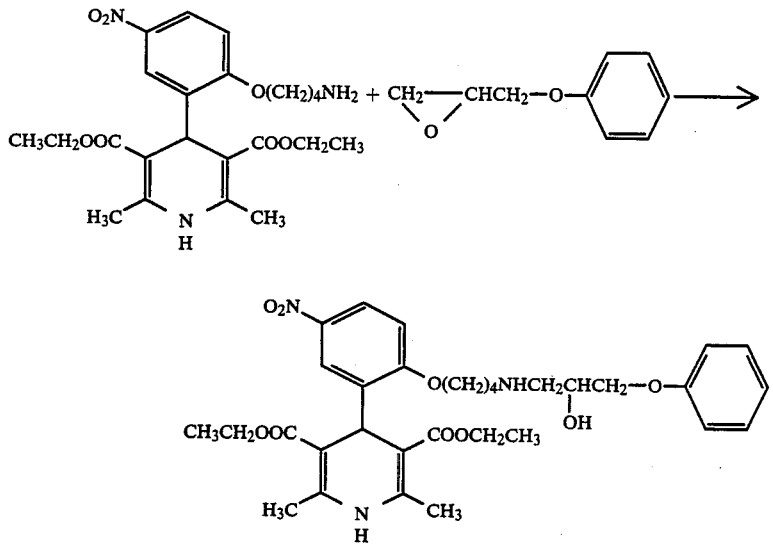

In 500 ml of methanol were dissolved 5.2 g of diethyl 4-[2-(4-aminobutoxy)-5-nitrophenyl]-2,6-dimethyl-1,4-dihydropyridine-3,5-dicarboxylate and 1.7 g of glycidyl phenyl ether, and the solution thus formed was refluxed under heating for 16 hours. The solvent was distilled off under reduced pressure. The residue was subjected to silica gel column chromatography, and the product was eluted with chlroform-methanol (95:5 v/v). Crude crystals were recrystallized from ethanol to give 2.2 g of diethyl 4-[2-[4-(2-hydroxy-3-phenoxypropylamino)-butoxy]-5-nitrophenyl]-2,6-dimethyl-1,4-dihydropyridine-3,5-dicarboxylate.

mp. 141°–143° C.

| Anal (C32H41N3O9) | | | |
|---|---|---|---|
| | C (%) | H (%) | N (%) |
| Cal | 62.83 | 6.76 | 6.87 |
| Fnd | 62.85 | 6.86 | 6.86 |

NMR (CDCl3). δ(ppm): 1.14 (6H, t), 1.5–2.0 (4H, m), 2.28 (6H, s), 5.24 (1H, s).

EXAMPLES 19–22

By following the same procedure as in Example 18, the following compounds were obtained.

EXAMPLE 19

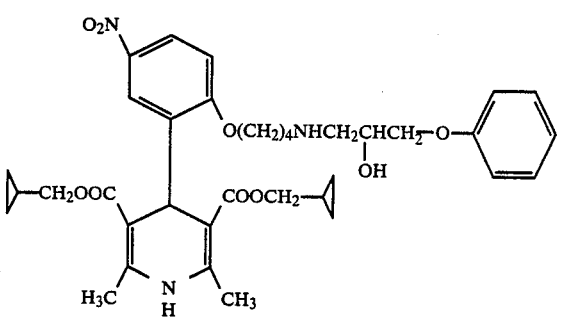

bis(cyclopropylmethyl) 4-[2-[4-(2-hydroxy-3-phenoxypropylamino)butoxy]-5-nitrophenyl]-2,6-dimethyl-1,4-dihydropyridine-3,5-dicarboxylate mp. 148°~151° C.

| Anal (C36H45N3O9) | | | |
|---|---|---|---|
| | C (%) | H (%) | N (%) |
| Cal | 65.14 | 6.83 | 6.33 |
| Fnd | 64.96 | 6.94 | 6.32 |

NMR (CDCl3). δ(ppm); 0~0.6 (8H, m), 0.8~1.3 (2H, m), 1.4~2.0 (4H, m), 2.30 (6H, m), 5.28 (1H, s).

EXAMPLE 20

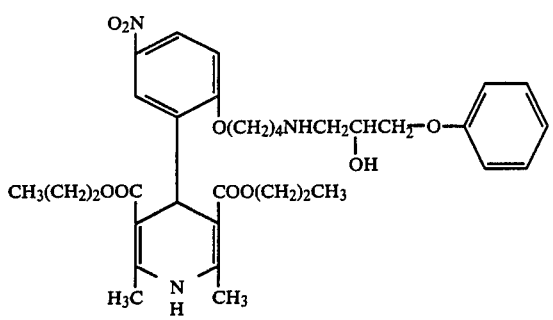

dipropyl
4-[2-[4-(2-hydroxy-3-phenoxypropylamino)butoxy]-5-nitrophenyl]-2,6-dimethyl-1,4-dihydropyridine-3,5-dicarboxylate mp. 148°~151° C.

| Anal ($C_{34}H_{45}N_3O_9$) | | | |
|---|---|---|---|
| | C (%) | H (%) | N (%) |
| Cal | 63.83 | 7.09 | 6.57 |
| Fnd | 63.60 | 7.01 | 6.50 |

NMR (CDCl$_3$). δ(ppm); 0.84 (6H, t), 1.2~2.0 (8H, m), 2.30 (6H, s), 5.28 (1H, s).

EXAMPLE 21

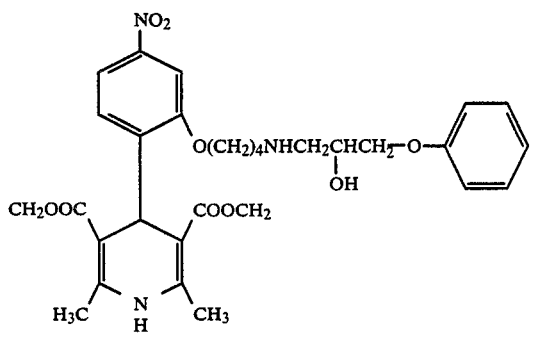

dimethyl
4-[2-[4-(2-hydroxy-3-phenoxypropylamino)butoxy]-4-nitrophenyl]-2,6-dimethyl-1,4-dihydropyridine-3,5-dicarboxylate mp. 122°~124° C.

| Anal ($C_{30}H_{37}N_3O_9.0.5H_2O$) | | | |
|---|---|---|---|
| | C (%) | H (%) | N (%) |
| Cal | 60.80 | 6.46 | 7.09 |
| Fnd | 60.71 | 6.42 | 7.04 |

NMR (CDCl$_3$). δ(ppm); 1.6~2.0 (4H, m), 2.30 (6H, s), 3.58 (6H, s), 5.32 (1H, s).

EXAMPLE 22

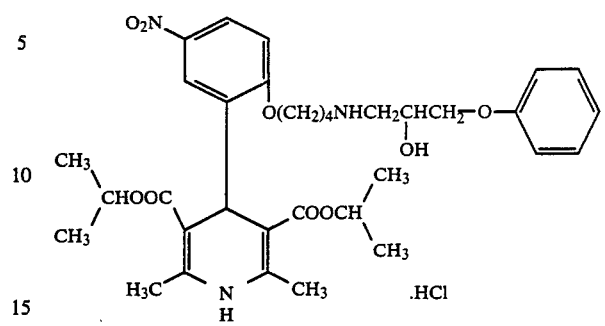

diisopropyl
4-[2-[4-(2-hydroxy-3-phenoxypropylamino)butoxy]-5-nitrophenyl]-2,6-dimethyl-1,4-dihydropyridine-3,5-dicarboxylate hydrochloride mp. 212°~213° C.

| Anal ($C_{34}H_{46}N_3O_9Cl$) | | | |
|---|---|---|---|
| | C (%) | H (%) | N (%) |
| Cal | 60.39 | 6.86 | 6.21 |
| Fnd | 60.19 | 6.92 | 6.24 |

NMR (DMSO-d$_6$). δ(ppm); 0.90 (6H, d), 1.16 (6H, d), 2.24 (6H, s), 3.32 (6H, s), 4.74 (2H, m), 5.04 (1H, s).

EXAMPLE 23

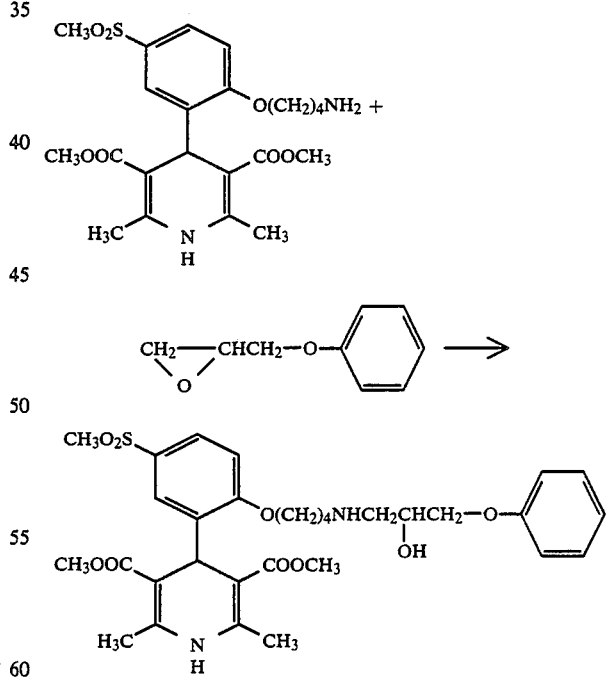

In 44 ml of methanol were dissolved 2.57 g of dimethyl 4-[2-(4-aminobutoxy)-5-methylsulfonylphenyl]-2,6-dimethyl-1,4-dihydropyridine-3,5-dicarboxylate (obtained in Reference Example 2) and 0.83 g of glycidyl phenyl ether, and the solution formed was allowed to react at room temperature for 43 hours and concentrated under reduced pressure. The residue was subjected to silica gel column chromatography, and the product was eluted with chloroform-methanol (95:5 v/v). Crude crystals were recrystallized from ethanol-ether to give 1.05 g of dimethyl 4-[2-[4-(2-hydroxy-3-phenoxypropylamino)butoxy]-5-methylsulfonylphenyl]-2,6-dimethyl-1,4-dihydropyridine-3,5-dicarboxylate.

mp. 145°-146° C.

| Anal ($C_{31}H_{40}N_2O_9S \cdot 0.5H_2O$) | | | |
|---|---|---|---|
| | C (%) | H (%) | N (%) | S (%) |
| Cal | 59.50 | 6.60 | 4.48 | 5.12 |
| Fnd | 59.60 | 6.63 | 4.29 | 5.28 |

NMR (CDCl$_3$). δ(ppm): 2.28 (6H, s), 2.98 (3H, s), 3.56 (6H, s), 5.28 (1H, s).

EXAMPLES 24-37

By following the same procedure as in Example 23, the following compounds were obtained.

EXAMPLE 24

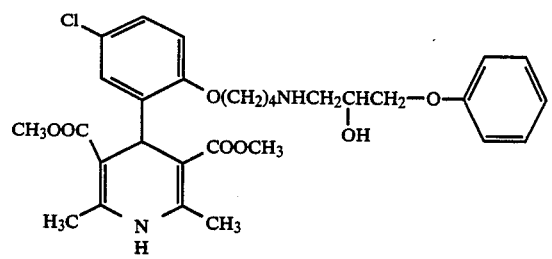

dimethyl 4-[5-chloro-2-[4-(2-hydroxy-3-phenoxypropylamino)butoxy]phenyl]-2,6-dimethyl-1,4-dihydropyridine-3,5-dicarboxylate amorphous powder

| Anal ($C_{30}H_{37}ClN_2O_7$) | | | |
|---|---|---|---|
| | C (%) | H (%) | N (%) |
| Cal | 62.88 | 6.51 | 4.89 |
| Fnd | 62.71 | 6.43 | 4.80 |

NMR (CDCl$_3$). δ(ppm); 1.5~1.9 (4H, m), 2.28 (6H, s), 3.60 (6H, s), 5.24 (1H, s).

EXAMPLE 25

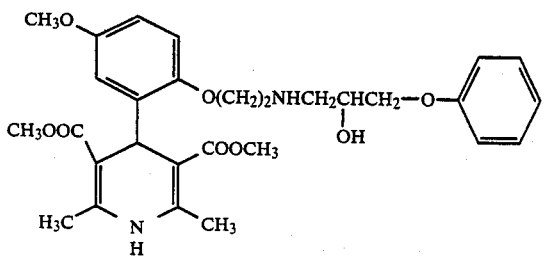

dimethyl 4-[2-[2-(2-hydroxy-3-phenoxypropylamino)ethoxy]-5-methoxyphenyl]-2,6-dimethyl-1,4-dihydropyridine-3,5-dicarboxylate mp. 141°~143° C.

| Anal ($C_{29}H_{36}N_2O_8$) | | | |
|---|---|---|---|
| | C (%) | H (%) | N (%) |
| Cal | 64.43 | 6.71 | 5.18 |
| Fnd | 64.09 | 6.68 | 5.08 |

NMR (CDCl$_3$). δ(ppm); 2.23 (6H, s), 3.56 (6H, s), 3.68 (3H, s), 5.28 (1H, s).

EXAMPLE 26

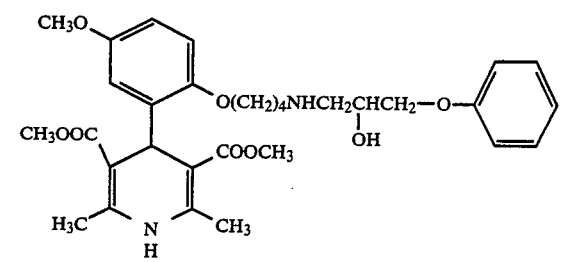

dimethyl 4-[2-[4-(2-hydroxy-3-phenoxypropylamino)butoxy]-5-methoxyphenyl]-2,6-dimethyl-1,4-dihydropyridine-3,5-dicarboxylate amorphous powder

| Anal ($C_{31}H_{40}N_2O_8 \cdot 0.5H_2O$) | | | |
|---|---|---|---|
| | C (%) | H (%) | N (%) |
| Cal | 64.46 | 7.15 | 4.85 |
| Fnd | 64.49 | 7.27 | 4.72 |

NMR (pyridine-d$_5$). δ(ppm); 2.51 (6H, s), 3.65 (9H, s. like), 5.85 (1H, s).

EXAMPLE 27

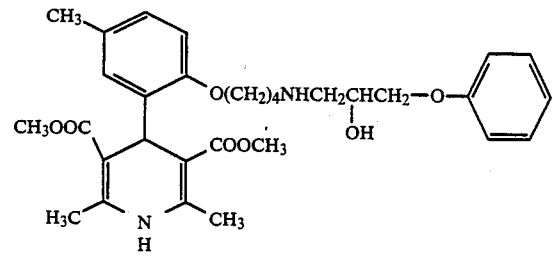

dimethyl 4-[2-[4-(2-hydroxy-3-phenoxypropylamino)butoxy]-5-methylphenyl]-2,6-dimethyl-1,4-dihydropyridine-3,5-dicarboxylate amorphous powder

| Anal (C₃₁H₄₀N₂O₇·0.5H₂O) | | | |
|---|---|---|---|
| | C (%) | H (%) | N (%) |
| Cal | 66.29 | 7.36 | 4.99 |
| Fnd | 66.38 | 7.36 | 4.95 |

NMR (CDCl₃). δ(ppm); 2.21 (3H, s), 2.27 (6H, s), 3.57 (6H, s), 5.22 (1H, s), 6.17 (1H, s).

EXAMPLE 28

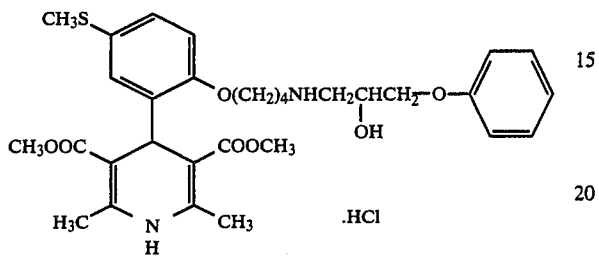

dimethyl 4-[2-[4-(2-hydroxy-3-phenoxypropylamino)butoxy]-5-methylthiophenyl]-2,6-dimethyl-1,4-dihydropyridine-3,5-dicarboxylate hydrochloride amorphous powder

| Anal (C₃₁H₄₀N₂O₇S·HCl 0.8H₂O) | | | | | |
|---|---|---|---|---|---|
| | C (%) | H (%) | N (%) | Cl (%) | S (%) |
| Cal | 58.58 | 6.76 | 4.41 | 5.58 | 5.04 |
| Fnd | 58.60 | 6.91 | 4.25 | 5.79 | 5.24 |

NMR (CDCl₃). δ(ppm); 2.30 (6H, s), 2.39 (3H, s), 3.54 (6H, s), 5.14 (1H, s).

EXAMPLE 29

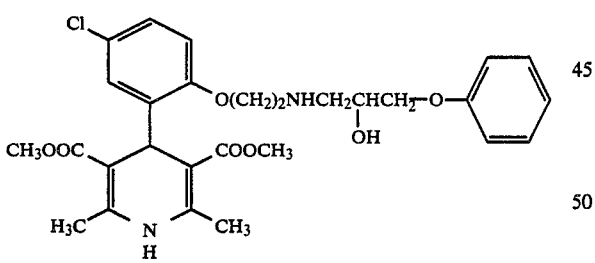

dimethyl 4-[5-chloro-2-[2-(2-hydroxy-3-phenoxypropylamino)ethoxy]phenyl]-2,6-dimethyl-1,4-dihydropyridine-3,5-dicarboxylate mp. 184°~186° C.

| Anal (C₂₈H₃₃ClN₂O₇) | | | |
|---|---|---|---|
| | C (%) | H (%) | N (%) |
| Cal | 61.70 | 6.10 | 5.14 |
| Fnd | 60.91 | 6.23 | 4.94 |

NMR (CDCl₃). δ(ppm); 2.30 (6H, s), 3.62 (6H, s), 5.26 (1H, s).

EXAMPLE 30

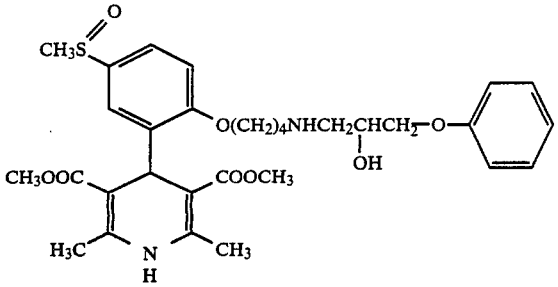

dimethyl 4-[2-[4-(2-hydroxy-3-phenoxypropylamino)butoxy]-5-methylsulfinylphenyl]-2,6-dimethyl-1,4-dihydropyridine-3,5-dicarboxylate mp. 83°~86° C.

| Anal (C₃₁H₄₀N₂O₈S·0.5H₂O) | | | | |
|---|---|---|---|---|
| | C (%) | H (%) | N (%) | S (%) |
| Cal | 61.07 | 6.78 | 4.59 | 5.26 |
| Fnd | 61.02 | 6.89 | 4.41 | 5.28 |

NMR (CDCl₃). δ(ppm); 2.28 (6H, s), 2.65 (3H, s), 3.55 (6H, s), 5.28 (1H, s).

EXAMPLE 31

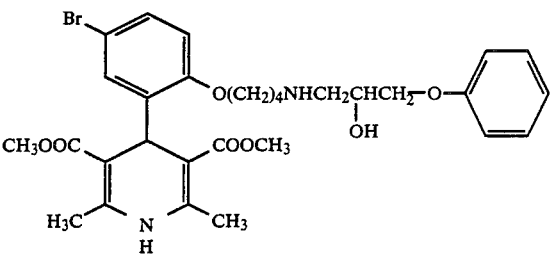

dimethyl 4-[5-bromo-2-[4-(2-hydroxy-3-phenoxypropylamino)butoxy]phenyl]-2,6-dimethyl-1,4-dihydropyridine-3,5-dicarboxylate mp. 83°~85° C.

| Anal (C₃₀H₃₇N₂O₇Br) | | | | |
|---|---|---|---|---|
| | C (%) | H (%) | N (%) | Br (%) |
| Cal | 58.35 | 6.04 | 4.54 | 12.94 |
| Fnd | 58.50 | 6.28 | 4.35 | 12.44 |

NMR (CDCl₃). δ(ppm); 2.27 (6H, s), 3.58 (6H, s), 5.21 (1H, s), 6.46 (1H, s).

EXAMPLE 32

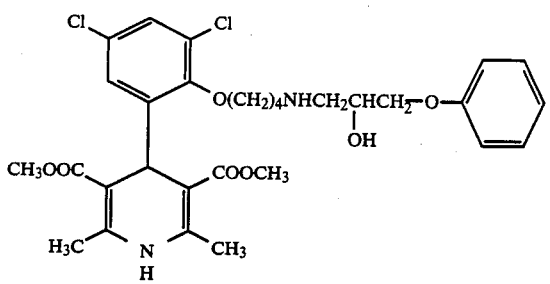

dimethyl
4-[3,5-dichloro-2-[4-(2-hydroxy-3-phenoxy-propylamino)butoxy]phenyl]-2,6-dimethyl-1,4-dihydropyridine-3,5-dicarboxylate mp. 72°~74° C.

| Anal ($C_{30}H_{36}N_2O_7Cl_2 \cdot H_2O$) | | | | |
|---|---|---|---|---|
| | C (%) | H (%) | N (%) | Cl (%) |
| Cal | 57.60 | 6.12 | 4.48 | 11.34 |
| Fnd | 57.90 | 6.35 | 4.33 | 11.42 |

NMR (CDCl$_3$). δ(ppm); 2.28 (6H, s), 3.62 (6H, s), 5.22 (1H, s), 6.07 (1H, s).

EXAMPLE 33

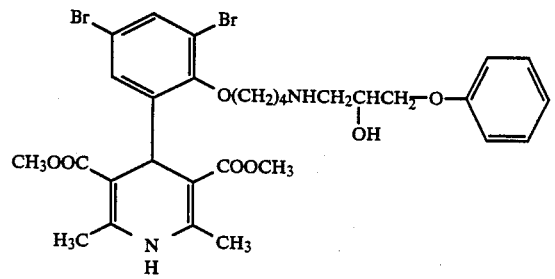

dimethyl
4-[3,5-dibromo-2-[4-(2-hydroxy-3-phenoxy-propylamino)butoxy]phenyl]-2,6-dimethyl-1,4-dihydropyridine-3,5-dicarboxylate amorphous powder

| Anal ($C_{30}H_{36}N_2O_7Br_2 \cdot 0.1H_2O$) | | | | |
|---|---|---|---|---|
| | C (%) | H (%) | N (%) | Br (%) |
| Cal | 51.61 | 5.23 | 4.01 | 22.89 |
| Fnd | 51.38 | 5.36 | 3.91 | 23.21 |

NMR (CDCl$_3$). δ(ppm); 2.28 (6H, s), 3.64 (6H, s), 5.26 (1H, s), 6.12 (1H, s).

EXAMPLE 34

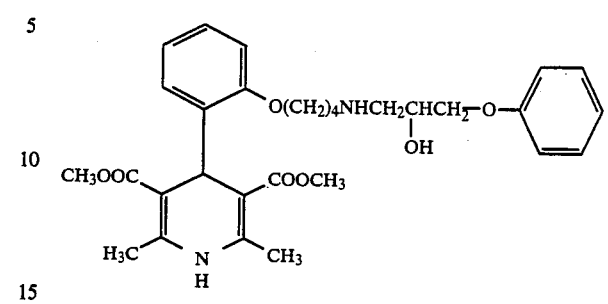

dimethyl
4-[o-[4-(2-hydroxy-3-phenoxypropylamino)butoxy]-phenyl]-2,6-dimethyl-1,4-dihydropyridine-3,5-dicarboxylate mp. 129°~130° C.

| Anal ($C_{30}H_{38}N_2O_7$) | | | |
|---|---|---|---|
| | C (%) | H (%) | N (%) |
| Cal | 66.90 | 7.11 | 5.20 |
| Fnd | 66.70 | 7.34 | 5.04 |

NMR (CDCl$_3$). δ(ppm); 1.5~1.9 (4H, m), 2.28 (6H, s), 3.56 (6H, s), 5.20 (1H, s).

EXAMPLE 35

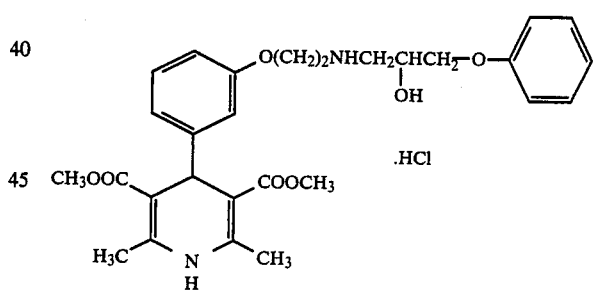

dimethyl
4-[m-[2-(2-hydroxy-3-phenoxypropylamino)ethoxy]-phenyl]-2,6-dimethyl-1,4-dihydropyridine-3,5-dicarboxylate hydrochloride mp. 136°~139° C.

| Anal ($C_{28}H_{34}N_2O_7 \cdot HCl$) | | | |
|---|---|---|---|
| | C (%) | H (%) | N (%) |
| Cal | 61.48 | 6.45 | 5.12 |
| Fnd | 61.27 | 6.44 | 5.09 |

NMR (CDCl$_3$). δ(ppm); 2.28 (6H, s), 3.60 (6H, s), 5.24 (1H, s).

EXAMPLE 36

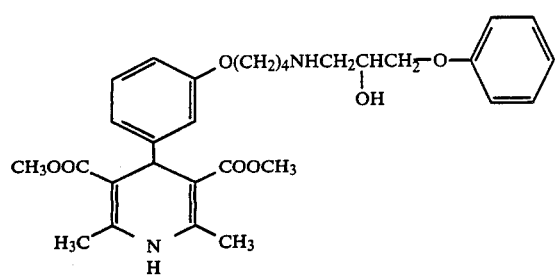

dimethyl
4-[m-[4-(2-hydroxy-3-phenoxypropylamino)butoxy]-
phenyl]-2,6-dimethyl-1,4-dihydropyridine-3,5-dicar-
boxylate mp. 106°~107.5° C.

|  | Anal ($C_{30}H_{38}N_2O_7 \cdot 0.5H_2O$) | | |
|---|---|---|---|
|  | C (%) | H (%) | N (%) |
| Cal | 65.80 | 7.18 | 5.12 |
| Fnd | 65.72 | 7.32 | 4.97 |

NMR (CDCl$_3$). δ(ppm); 2.31 (6H, s), 3.65 (6H, s), 5.00 (1H, s), 6.04 (1H, s).

EXAMPLE 37

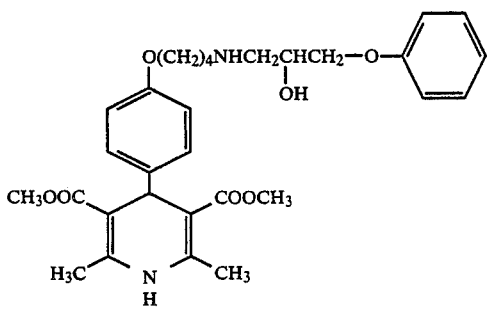

dimethyl
4-[p-[4-(2-hydroxy-3-phenoxypropylamino)butoxy]-
phenyl]-2,6-dimethyl-1,4-dihydropyridine-3,5-dicar-
boxylate mp. 83°~85° C.

|  | Anal ($C_{30}H_{38}N_2O_7$) | | |
|---|---|---|---|
|  | C (%) | H (%) | N (%) |
| Cal | 66.90 | 7.11 | 5.20 |
| Fnd | 66.64 | 7.20 | 5.08 |

NMR (CDCl$_3$). δ(ppm); 2.31 (6H, s), 3.64 (6H, s), 4.95 (1H, s), 5.78 (1H, s).

EXAMPLE 38

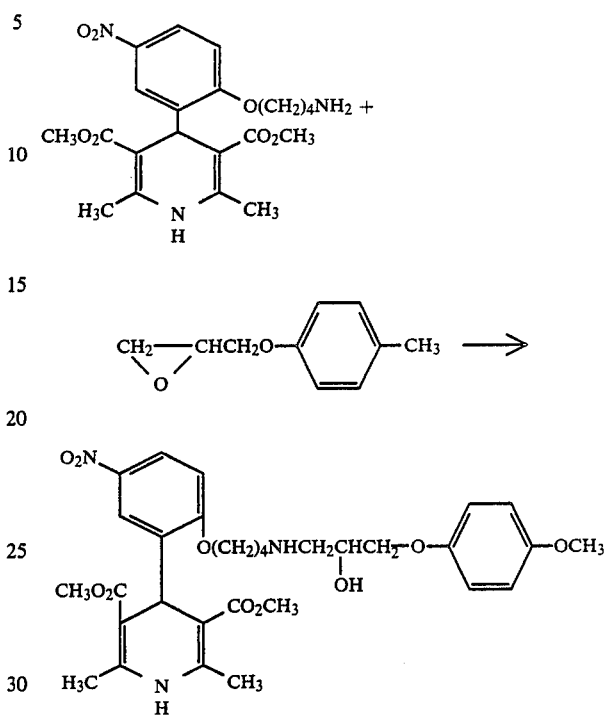

In 200 ml of methanol were dissolved 2 g of dimethyl 4-[2-(4-aminobutoxy)-5-nitrophenyl]-2,6-dimethyl-1,4-dihydropyridine-3,5-dicarboxylate and 0.84 g of glycidyl 4-methoxyphenyl ether, and the solution was refluxed under heating for 3 hours. The solvent was distilled off under reduced pressure. The residue was subjected to silica gel column chromatography, and the product was eluted with chloroform-methanol (95:5 v/v). Crude crystals were recrystallized from a mixture of methanol and ethyl ether to give 0.85 g of dimethyl 4-[2-[4-[2-hydroxy-3-(p-methoxyphenoxy)-propylamino]butoxy]-5-nitrophenyl]-2,6-dimethyl-1,4-dihydropyridine-3,5-dicarboxylate.

mp. 154°-155° C.

|  | Anal ($C_{31}H_{39}N_3O_{10}$) | | |
|---|---|---|---|
|  | C (%) | H (%) | N (%) |
| Cal | 60.68 | 6.41 | 6.85 |
| Fnd | 60.57 | 6.49 | 6.75 |

NMR (CDCl$_3$). δ(ppm): 2.28 (6H, s), 3.56 (6H, s), 3.76 (3H, s), 5.30 (1H, s).

EXAMPLES 39-45

By following the same procedure as in Example 38, the following compounds were obtained.

EXAMPLE 39

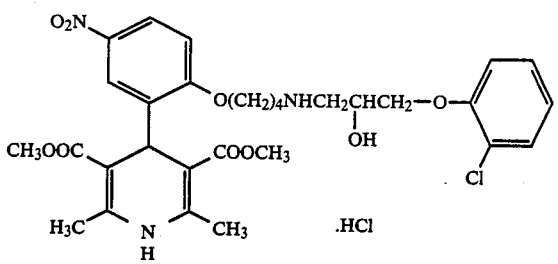

dimethyl
4-[2-[4-[3-(o-chlorophenoxy)-2-hydroxypropylamino]-
butoxy]-5-nitrophenyl]-2,6-dimethyl-1,4-dihydropyri-
dine-3,5-dicarboxylate hydrochloride amorphous powder

| Anal ($C_{30}H_{36}ClN_3O_7 \cdot HCl$) | | | |
|---|---|---|---|
| | C (%) | H (%) | N (%) |
| Cal | 57.88 | 5.99 | 6.75 |
| Fnd | 58.13 | 5.87 | 6.69 |

NMR (DMSO-$d_6$). δ(ppm); 1.4~1.8 (4H, m), 2.32 (6H, s), 3.64 (6H, s), 5.26 (1H, s).

EXAMPLE 40

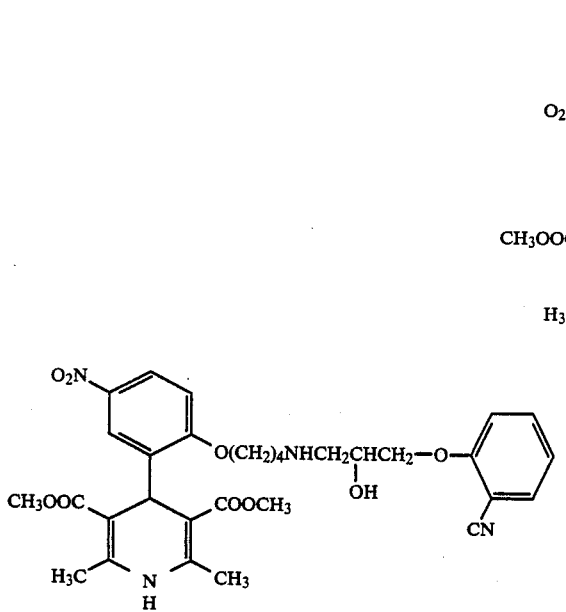

dimethyl
4-[2-[4-[3-(o-cyanophenoxy)-2-hydroxypropylamino]-
butoxy]-5-nitrophenyl]-2,6-dimethyl-1,4-dihydropyri-
dine-3,5-dicarboxylate mp. 169°~171° C.

| ($C_{31}H_{36}N_4O_9$) | | | |
|---|---|---|---|
| | C (%) | H (%) | N (%) |
| Cal | 61.18 | 5.96 | 9.21 |
| Fnd | 61.06 | 5.91 | 9.08 |

NMR (CDCl$_3$). δ(ppm); 2.32 (6H, s), 2.76 (2H, t), 3.56 (6H, s), 5.24 (1H, s).

EXAMPLE 41

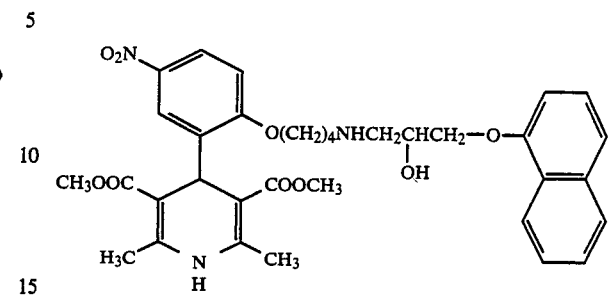

dimethyl
4-[2-[4-[2-hydroxy-3-(1-naphthyloxy)propylamino]-
butoxy]-5-nitrophenyl-2,6-dimethyl-1,4-dihydropyri-
dine-3,5-dicarboxylate mp. 180°~181° C.

| Anal ($C_{34}H_{39}N_3O_9$) | | | |
|---|---|---|---|
| | C (%) | H (%) | N (%) |
| Cal | 64.44 | 6.20 | 6.63 |
| Fnd | 64.17 | 6.35 | 6.46 |

NMR (CDCl$_3$). δ(ppm); 2.26 (6H, s), 3.34 (6H, s), 5.30 (1H, s).

EXAMPLE 42

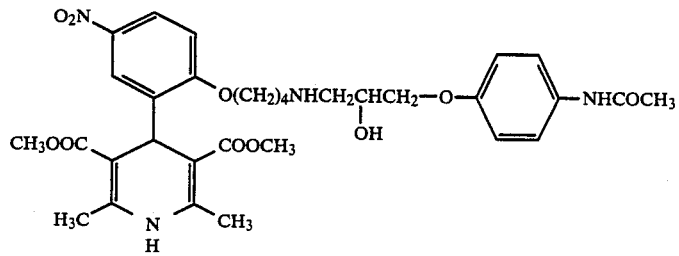

dimethyl
4-[2-[4-[3-(p-acetamidophenoxy)-2-hydroxy-
propylamino]butoxy]-5-nitrophenyl]-2,6-dimethyl-1,4-
dihydropyridine-3,5-dicarboxylate mp. 175°~176° C.

| Anal ($C_{32}H_{40}N_4O_{10}$) | | | |
|---|---|---|---|
| | C (%) | H (%) | N (%) |
| Cal | 59.99 | 6.29 | 8.74 |
| Fnd | 59.98 | 6.39 | 8.64 |

NMR (CDCl$_3$+DMSO-$d_6$) δ(ppm); 2.08 (3H, s), 2.28 (6H, s), 3.54 (6H, s), 5.28 (1H, s).

EXAMPLE 43

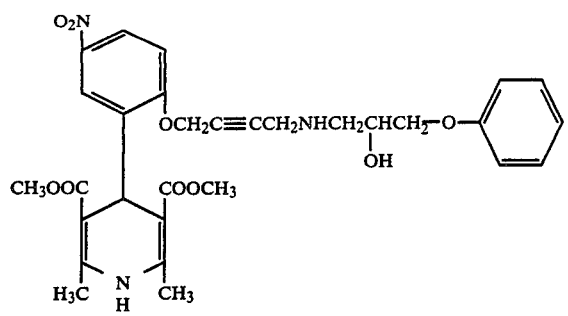

dimethyl 4-[2-[4-(2-hydroxy-3-phenoxypropylamino)-2-butynyloxy]-5-nitrophenyl]-2,6-dimethyl-1,4-dihydropropyridine-3,5-dicarboxylate amorphous powder

| | Anal (C30H33N3O9.2H2O) | | |
|---|---|---|---|
| | C (%) | H (%) | N (%) |
| Cal | 58.53 | 6.06 | 6.83 |
| Fnd | 58.73 | 6.35 | 7.09 |

NMR (CDCl3). δ(ppm); 2.30 (6H, s), 3.60 (6H, s), 4.00 (2H, s), 5.30 (1H, s).

EXAMPLE 44

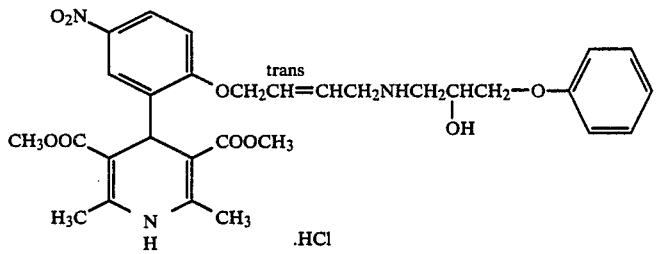

dimethyl 4-[2-[(E)-4-(2-hydroxy-3-phenoxypropylamino)-2-butenyloxy]-5-nitrophenyl)-2,6-dimethyl-1,4-dihydropyridine-3,5-dicarboxylate hydrochloride mp. 171°~173° C.

| | Anal (C30H36N3O9Cl) | | |
|---|---|---|---|
| | C (%) | H (%) | N (%) |
| | 58.30 | 5.87 | 6.80 |

-continued

| | Anal (C30H36N3O9Cl) | | |
|---|---|---|---|
| | C (%) | H (%) | N (%) |
| | 57.97 | 5.95 | 6.78 |

NMR (DMSO-d6). δ(ppm); 2.24 (6H, s), 3.46 (6H, s), 5.24 (1H, s).

EXAMPLE 45

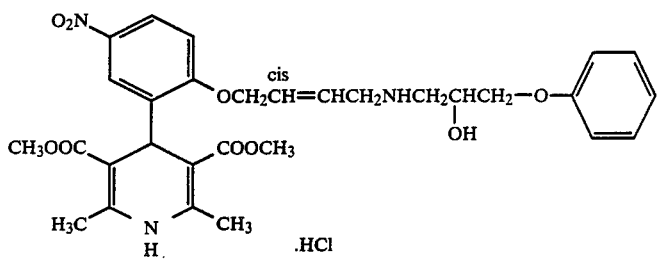

dimethyl 4-[2-[(Z)-4-(2-hydroxy-3-phenoxypropylamino)-2-butenyloxy]-5-nitrophenyl]-2,6-dimethyl-1,4-dihydropyridine-3,5-dicarboxylate hydrochloride mp. 191°~193° C.

| | Anal (C30H36N3O9Cl) | | |
|---|---|---|---|
| | C (%) | H (%) | N (%) |
| Cal | 58.30 | 5.87 | 6.80 |
| Fnd | 58.05 | 5.87 | 6.88 |

NMR (CDCl3). δ(ppm); 2.28 (6H, s), 3.58 (6H, s), 4.70 (2H, d), 5.34 (1H, s).

EXAMPLE 46

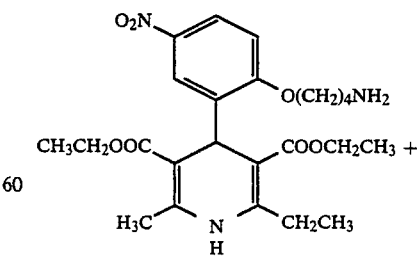

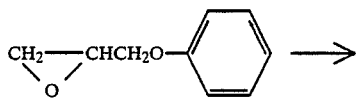

-continued

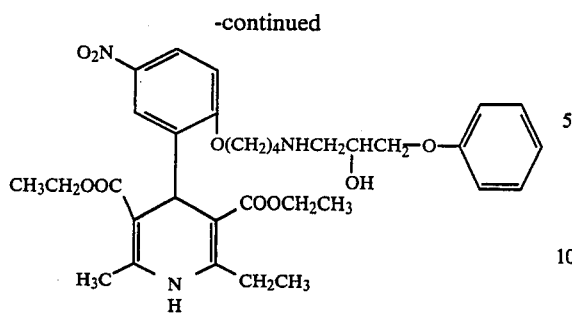

In 46 ml of methanol were dissolved 4.62 g of diethyl 4-[2-(4-aminobutoxy)-5-nitrophenyl]-2-ethyl-6-methyl-1,4-dihydropyridine-3,5-dicarboxylate and 1.46 g of glycidyl phenyl ether, and the solution formed was refluxed under heating for 15 hours. After cooling the reaction solution, the solution was concentrated under reduced pressure. The residue was subjected to silica gel column chromatography, and the product was eluted with chloroform-methanol (95:5 v/v). Crude crystals were recrystallized from ethanol to give 1.22 g of diethyl 2-ethyl-4-[2-[4-(2-hydroxy-3-phenoxypropylamino)butoxy]-5-nitrophenyl]-6-methyl-1,4-dihydropyridine-3,5-dicarboxylate.
mp. 159.0°–159.5° C.

|  | Anal ($C_{33}H_{43}N_3O_9$) | | |
|---|---|---|---|
|  | C (%) | H (%) | N (%) |
| Cal | 63.35 | 6.93 | 6.72 |
| Fnd | 63.18 | 6.78 | 6.62 |

NMR (CDCl$_3$). δ(ppm): 2.30 (3H, s), 5.30 (1H, s), 6.57 (1H, s).

EXAMPLE 47

Medical composition

Formulation for 1,000 tablets:

| Active compound | 100 g |
|---|---|
| Starch | 185 g |
| Lactose | 25 g |
| Magnesium stearate | 1.5 g |

The above components were granulated using a starch paste as a binder and then molded is conventional manner.

REFERENCE EXAMPLE 4

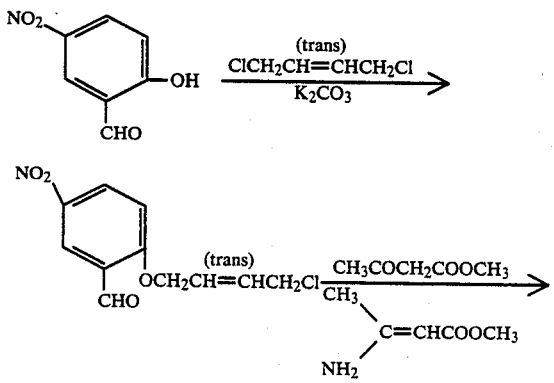

-continued

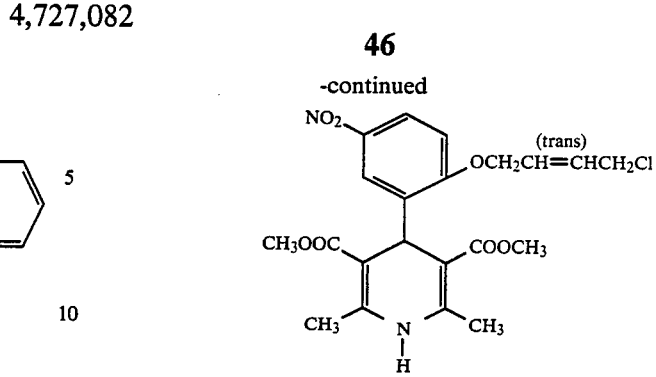

(1) A solution of 8 g of 5-nitrosalicylaldehyde, 30.8 g of trans-1,4-dichloro-2-butene and 13.2 g of potassium carbonate in 35 ml of dimethylformamide was stirred at room temperature for 19 hours, and further stirred at 80°–87° C. (outside temperature) for 2 hours. The mixture was allowed to cool, poured into 80 ml of water, and extracted with chloroform. The extract (organic layer separated) was concentrated under reduced pressure. The residue was subjected to column chromatography on silica gel. The product was eluted with benzene to give 5.3 g of 2-[(E)-4-chloro-2-butenyloxy]-5-nitrobenzaldehyde. (mp. 65°–66° C.).

(2) 5.2 g of 2-[(E)-4-chloro-2-butenyloxy]-5-nitrobenzaldehyde, 2.4 g of methyl acetoacetate and 2.3 g of methyl 3-aminocrotonate was dissolved in 30 ml of iso-propanol, and the solution obtained was refluxed for 3.5 hours under heating. After cooling, the precipitated crystals were collected by filtration to give 4.4 g of dimethyl 4-[2-[(E)-4-chloro-2-butenyloxy]-5-nitrophenyl]-2,6-dimethyl-1,4-dihydropyridine-3,5-dicarboxylate. (mp. 206°–207° C.). The product obtained was used directly for the next process without purification.

EXAMPLE 48

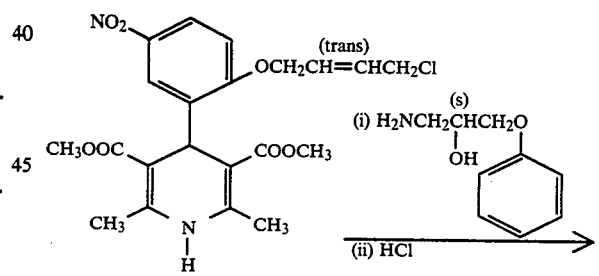

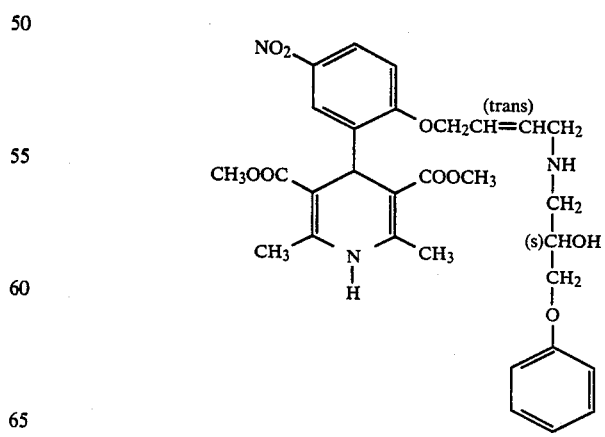

3.1 g of dimethyl 4-[2-[(E)-4-chloro-2-butenyloxy]-5-nitrophenyl]-2,6-dimethyl-1,4-dihydropyridine-3,5- dicarboxylate and 5.8 g (S)-2-hydroxy-3-phenoxypropylamine were dissolved in 35 ml of acetonitrile, and the resultant solution was refluxed under heating for 2 hours. The reaction solution was concentrated under reduced pressure, and the residue was dissolved in 30 ml of chloroform. After washing the solution with water three times, the organic layer was concentrated under reduced pressure. The residue obtained was subjected to column chromatography on silica gel. The product was eluted with chloroform-methanol (95:5 V/V), was converted to HCl salt, and then was treated with ether-ethyl acetate to give 1.8 g of dimethyl 4-[2-[(E)-4-[[(S)-2-hydroxy-3-phenoxypropyl]amino]-2-butenyloxy]-5-nitrophenyl]-2,6-dimethyl-1,4-dihydropyridine-3,5-dicarboxylate HCl salt.

|  | Anal (C$_{30}$H$_{35}$N$_3$O$_9$.HCl) | | |
|---|---|---|---|
|  | C (%) | H (%) | N (%) |
| Cal | 58.30 | 5.87 | 6.80 |
| Fnd | 58.10 | 6.11 | 6.84 |

NMR (CDCl$_3$) [free compound]. δ(ppm); 2.29 (6H, s), 3.57 (6H, s), 5.31 (1H, s), 5.8–6.0 (2H, m).

Mass spectrum (FAB) [free compound]. 582 (M$^+$+1), 224.

EXAMPLE 49

Dimethyl 4-[2-[4-[3-(p-cyanophenoxy)-2-hydroxypropylamino]-butoxy-5-nitrophenyl-2,6-dimethyl-1,4-dihydropyridine-3,5-dicarboxylate

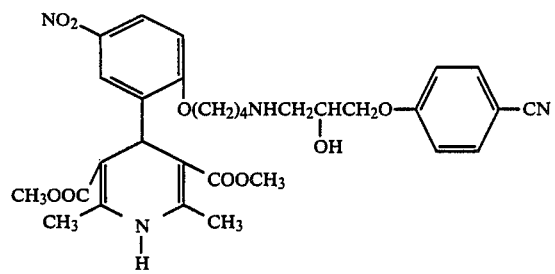

mp. 164°–165° C.

|  | Anal (C$_{31}$H$_{36}$N$_4$O$_9$) | | |
|---|---|---|---|
|  | C (%) | H (%) | N (%) |
| Cal | 61.18 | 5.96 | 9.21 |
| Fnd | 60.99 | 5.79 | 9.38 |

NMR (CDCl$_3$). δ(ppm); 1.6–2.0 (4H, m), 2.32 (6H, s), 3.72 (6H, s), 5.30 (1H, s).

EXAMPLE 50

Dimethyl 4-[5-fluoro-2-[4-[[2-hydroxy-3-phenoxypropyl]-amino]butoxy]phenyl]-2,6-dimethyl-1,4-dihydropyridine-3,5-dicarboxylate, HCl salt

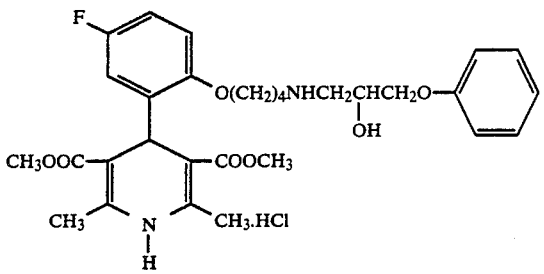

mp. 113°–115° C.

|  | Anal (C$_{30}$H$_{37}$FN$_2$O$_7$.HCl) | | | |
|---|---|---|---|---|
|  | C (%) | H (%) | N (%) | Cl (%) |
| Cal | 60.75 | 6.46 | 4.72 | 5.98 |
| Fnd | 60.44 | 6.57 | 4.63 | 5.94 |

NMR (CDCl$_3$). δ(ppm); 2.29 (6H, s), 3.54 (6H, s), 5.13 (1H, s).

EXAMPLE 51

Dimethyl 4-[2-[4-[[2-hydroxy-3-phenoxypropyl]amino]butoxy]-5-isopropylphenyl]-2,6-dimethyl-1,4-dihydropyridine-3,5-dicarboxylate, HCl salt

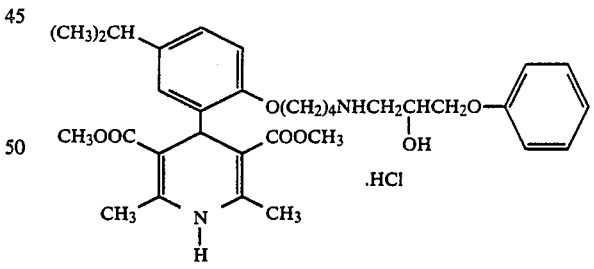

mp. 160°–162° C.

|  | Anal (C$_{33}$H$_{44}$N$_2$O$_7$.HCl) | | | |
|---|---|---|---|---|
|  | C (%) | H (%) | N (%) | Cl (%) |
| Cal | 64.22 | 7.35 | 4.54 | 5.74 |
| Fnd | 64.01 | 7.48 | 4.52 | 5.93 |

NMR (CDCl$_3$). δ(ppm); 1.15 (6H, d), 2.26 (6H, s), 3.46 (6H, s), 5.07 (1H, s).

EXAMPLE 52

Dimethyl 4-[5-ethoxy-2-[4-[[(s)-2-hydroxy-3-phenoxypropyl]amino]butoxy]phenyl]-2,6-dimethyl-1,4-dihydropyridine-3,5-dicarboxylate

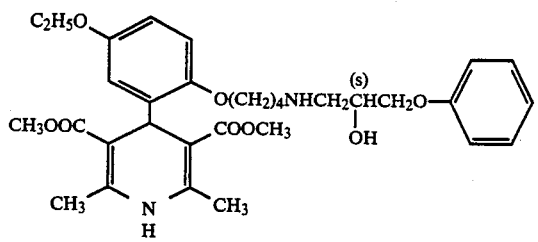

mp. 149°–150° C.

| Anal (C$_{32}$H$_{42}$N$_2$O$_8$:0.3H$_2$O) | | | |
|---|---|---|---|
| | C (%) | H (%) | N (%) |
| Cal | 65.36 | 7.30 | 4.76 |
| Fnd | 65.40 | 7.34 | 4.56 |

NMR (CDCl$_3$). δ(ppm); 1.38 (3H, t), 2.28 (6H, s), 3.59 (6H, s), 5.22 (1H, s).
[α]$_D^{24}$ −3.1° (c=0.67, chloroform)

EXAMPLE 53

Dimethyl 4-[2-[4-[[(s)-2-hydroxy-3-phenoxypropyl]amino]-2-butynyloxy]-5-methoxyphenyl]-2,6-dimethyl-1,4-dihydropyridine-3,5-dicarboxylate, HCl salt

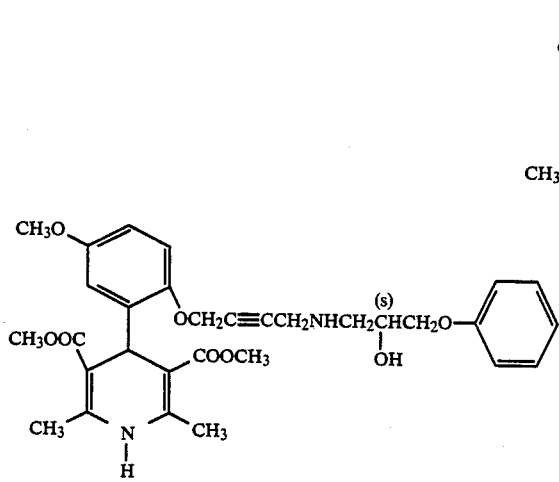

Amorphous powder

| Anal (C$_{31}$H$_{35}$N$_2$O$_8$.HCl:0.7H$_2$O) | | | |
|---|---|---|---|
| | C (%) | H (%) | N (%) |
| Cal | 60.77 | 6.15 | 4.57 |
| Fnd | 60.75 | 6.39 | 4.64 |

NMR (CDCl$_3$) [free compound]. δ(ppm); 2.28 (6H, s), 5.17 (1H, s).
[α]$_D^{24}$ −7.9° (c=0.98, methanol)

EXAMPLE 54

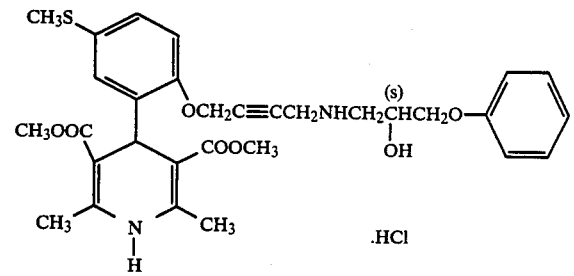

Dimethyl 4-[2-[4-[[(s)-2-hydroxy-3-phenoxypropyl]amino]-2-butynyloxy]-5-(methylthio)phenyl]-2,6-dimethyl-1,4-dihydropyridine-3,5-dicarboxylate, HCl salt Amorphous powder

| Anal (C$_{31}$H$_{36}$N$_2$O$_7$S.HCl.H$_2$O) | | | | | |
|---|---|---|---|---|---|
| | S (%) | C (%) | H (%) | N (%) | Cl (%) |
| Cal | 5.05 | 58.62 | 6.19 | 4.41 | 5.58 |
| Fnd | 4.93 | 58.70 | 6.28 | 4.29 | 5.65 |

NMR (DMSO-d$_6$). δ(ppm); 2.21 (6H, s), 2.33 (3H, s), 3.48 (6H, s), 4.78 (2H, m), 5.08 (1H, s).

EXAMPLE 55

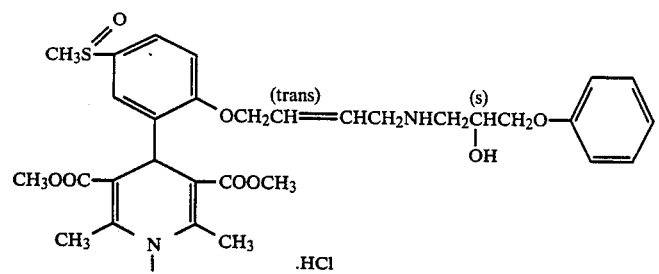

Dimethyl 4-[2-[(E)-4-[[(s)-2-hydroxy-3-phenoxypropyl]amino]-2-butenyloxy]-5-(methylsulfinyl)phenyl]-2,6-dimethyl-1,4-dihydropyridine-3,5-dicarboxylate, HCl salt Amorphous powder

| Anal (C$_{31}$H$_{38}$N$_2$O$_8$S.HCl.2H$_2$O) | | | | |
|---|---|---|---|---|
| | C (%) | H (%) | N (%) | S (%) |
| Cal | 55.47 | 6.46 | 4.17 | 4.78 |
| Fnd | 55.63 | 6.48 | 3.98 | 4.89 |

NMR (CDCl₃). δ(ppm); 2.39 (6H, s), 2.71 (3H, s), 3.51 (6H, s), 5.15 (1H, s).

EXAMPLE 56

Dimethyl 4-[2-[(E)-4-[[(s)-2-hydroxy-3-phenoxypropyl]-amino]-2-butenyloxy]-5-methoxyphenyl]-2,6-dimethyl-1,4-dihydropyridine-3,5-dicarboxylate, HCl salt

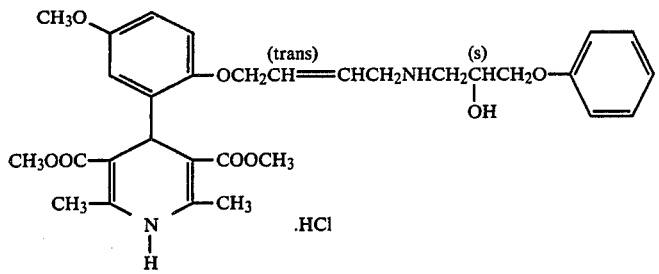

Amorphous powder

| Anal (C₃₁H₃₈N₂O₈.HCl) | | | |
|---|---|---|---|
| | C (%) | H (%) | N (%) |
| Cal | 61.74 | 6.52 | 4.64 |
| Fnd | 61.51 | 6.66 | 4.78 |

NMR (CDCl₃) [free compound]. δ(ppm); 2.25 (6H, s), 5.23 (1H, s), 5.8–6.95 (2H, m).
[α]$_D^{24}$ −7.3° (c=1, methanol)

EXAMPLE 57

Dimethyl 4-[5-ethoxy-2-[(E)-[[(s)-2-hydroxy-3-phenoxypropyl]amino]-2-butenyloxy]phenyl]-2,6-dimethyl-1,4-dihydropyridine-3,5-dicarboxylate, HCl salt

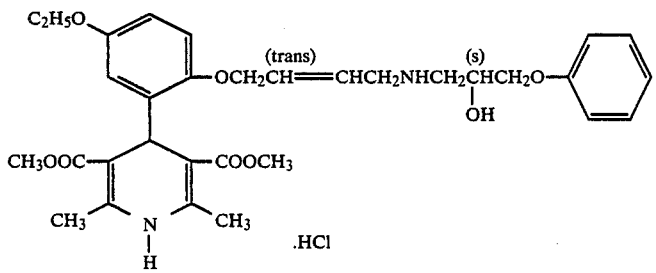

mp. 150°–153.5° C.

| Anal (C₃₂H₄₀N₂O₈.HCl) | | | |
|---|---|---|---|
| | C (%) | H (%) | N (%) |
| Cal | 62.28 | 6.70 | 4.54 |
| Fnd | 62.09 | 7.01 | 4.47 |

NMR (CDCl₃) [free compound]. δ(ppm); 1.37 (3H, t), 5.23 (1H, s), 2.27 (6H, s), 5.8–5.95 (2H, m), 3.59 (6H, s).
[α]$_D^{24}$ −8.4° (c=0.96, methanol)

EXAMPLE 58

Dimethyl 4-[2-[(E)-4-[[(s)-2-hydroxy-3-phenoxypropyl]amino]-2-butenyloxy]-5-methylthiophenyl]-2,6-dimethyl-1,4-dihydropyridine-3,5-dicarboxylate

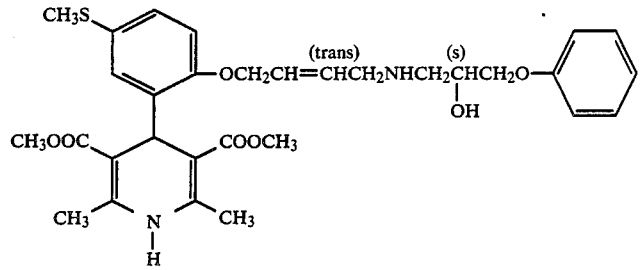

Amorphous powder

| Anal (C₃₁H₃₈N₂O₇S.H₂O) | | | | |
|---|---|---|---|---|
| | C (%) | H (%) | N (%) | S (%) |
| Cal | 61.98 | 6.71 | 4.66 | 5.34 |
| Fnd | 61.93 | 6.41 | 4.53 | 5.59 |

NMR (CDCl₃). δ(ppm); 2.28 (6H, s), 2.41 (3H, s), 3.59 (6H, s), 4.46 (2H, m), 5.20 (1H, s), 5.86 (2H, m).

EXAMPLE 59

Dimethyl 4-[2-(E)-4-[[(s)-2-hydroxy-3-phenoxypropyl]amino]-2-butenyloxy]-5-methylsulfonylphenyl]-2,6-dimethyl-1,4-dihydropyridine-3,5-dicarboxylate, HCl salt

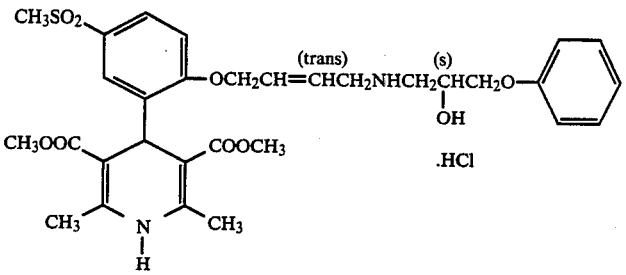

mp. 123°–126° C.

| Anal (C31H38N2O9S.HCl.0.5H2O) | | | | | |
|---|---|---|---|---|---|
| | C (%) | H (%) | N (%) | Cl (%) | S (%) |
| Cal | 56.40 | 6.11 | 4.24 | 5.37 | 4.86 |
| Fnd | 56.19 | 6.04 | 4.06 | 5.56 | 4.96 |

NMR (DMSO.d6). δ(ppm); 2.22 (6H, s), 3.08 (3H, s), 3.45 (6H, s), 4.66 (2H, m), 5.19 (1H, s), 6.07 (2h, m). [α]$_D^{18}$ −10.1 (c=0.62, methanol)

EXAMPLE 60

Dimethyl 4-[2-[4-[[3-(p-chlorophenoxy)-2-hydroxypropyl]amino]butoxy]-5-nitrophenyl]-2,6-dimethyl-1,4-dihydropyridine-3,5-dicarboxylate

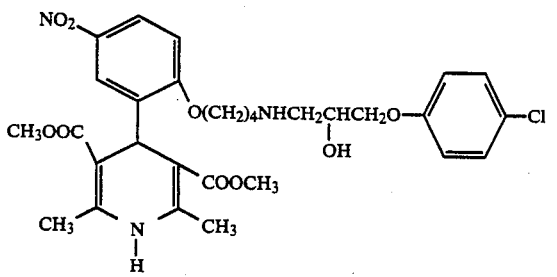

mp. 178°–179° C.

| Anal (C30H36N3O9Cl) | | | |
|---|---|---|---|
| | C (%) | H (%) | N (%) |
| Cal | 58.30 | 5.87 | 6.80 |

-continued

| Anal (C30H36N3O9Cl) | | | |
|---|---|---|---|
| | C (%) | H (%) | N (%) |
| Fnd | 58.12 | 5.74 | 6.85 |

NMR (CDCl3). δ(ppm); 2.32 (6H, s), 3.58 (6H, s), 5.30 (1H, s).

EXAMPLE 61

Dimethyl 4-[2-[(E)-4-[[3-(o-cyanophenoxy)-2-hydroxypropyl]amino]-2-butenyloxy]-5-nitrophenyl]-2,6-dimethyl-1,4-dihydropyridine-3,5-dicarboxylate

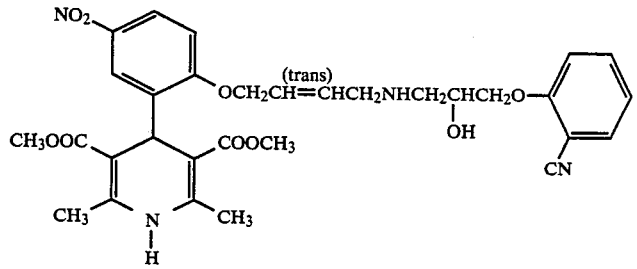

mp. 168°–169° C.

| Anal (C31H34N4O9) | | | |
|---|---|---|---|
| | C (%) | H (%) | N (%) |
| Cal | 61.38 | 5.65 | 9.24 |
| Fnd | 61.11 | 5.60 | 8.95 |

NMR (CDCl3). δ(ppm); 2.28 (6H, s), 3.56 (6H, s), 5.26 (1H, s), 5.75–5.95 (2H, m).

EXAMPLE 62

Dimethyl 4-[2-[4-[2-hydroxy-3-(o-methoxyphenoxy)-propylamino]butoxy]-5-nitrophenyl]-2,6-dimethyl-1,4-dihydropyridine-3,5-dicarboxylate

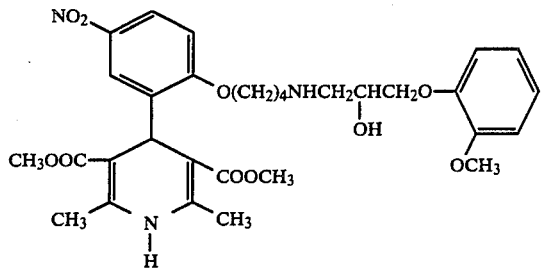

mp. 137°–138° C.

|  | Anal (C$_{31}$H$_{39}$N$_3$O$_{10}$) | | |
|---|---|---|---|
|  | C (%) | H (%) | N (%) |
| Cal | 60.67 | 6.41 | 6.85 |
| Fnd | 60.51 | 6.48 | 6.57 |

NMR (CDCl$_3$). δ(ppm); 2.28 (6H, s), 3.56 (6H, s), 3.84 (3H, s), 5.28 (1H, s).

We claim:

1. A dihydropyridine compound of the following general formula (I) or a salt thereof:

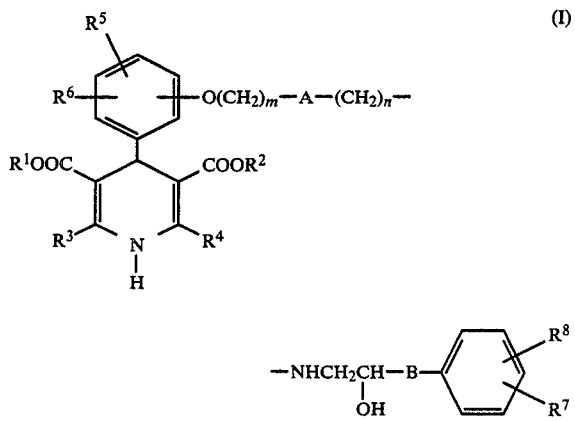

wherein R$^1$ and R$^2$, which are the same or different, each represents a C$_1$ to C$_{10}$ alkyl group, a lower alkyl group which is interrupted by oxygen atom(s), or a lower alkyl group substituted by C$_3$ to C$_6$ alicyclic group(s); R$^3$ and R$^4$, which are the same or different, each represents a lower alkyl group; R$^5$ and R$^6$, which are the same or different, each represents a hydrogen atom, a nitro group, a halogen atom, a lower alkyl group, a lower alkoxy group, a lower alkylthio group, a lower alkylsulfonyl group, or a lower alkylsulfinyl group; R$^7$ and R$^8$, which are the same or different, each represents a hydrogen atom, a halogen atom, a cyano group, a lower alkoxy group or a lower alkanoylamino group, or R$^7$ may combine with R$^8$ to fom a naphthyl group together with the adjacent phenyl group; A represents a single bond, a vinylene group (—CH=CH—), or a ethynylene group (—C≡C—); B represents a single bond or —CH$_2$O—; and m and n, which are the same or different, each represents 0 or an integer of 1 to 5.

2. A compound according to claim 1 wherein R$^1$ and R$^2$ are the same or different lower alkyl groups; R$^7$ is a hydrogen atom; and R$^8$ is a hydrogen atom.

3. A compound according to claim 1 wherein R$^1$ and R$^2$ are the same or different lower alkyl groups; R$^5$ and R$^6$, which may be the same or different, each represents a hydrogen atom, or a nitro group; B is —CH$_2$O—; R$^7$ represents a hydrogen atom; and R$^8$ represents a hydrogen atom.

4. A compound according to claim 1 which is dimethyl 4-[2-[4-(2-hydroxy-3-phenoxypropylamino)-butoxy]-5-nitrophenyl]-2,6-dimethyl-1,4-dihydropyridine-3,5-dicarboxylate or a salt thereof.

5. A compound of claim 1 which is (S)-(−)-dimethyl 4-[2-[4-(2-hydroxy-3-phenoxypropylamino)butoxy]-5-nitrophenyl]-2,6-dimethyl-1,4-dihydropyridine-3,5-dicarboxylate or a salt thereof.

6. A compound of claim 1 in which R-(+)-dimethyl 4-[2-[4-(2-hydroxy-3-phenoxypropylamino)butoxy]-5-nitrophenyl]-2,6-dimethyl-1,4-dihydropyridine-3,5-dicarboxylate or a salt thereof.

7. A pharmaceutical composition comprising as the active ingredient thereof, from about 1 to about 200 milligrams of a compound of claim 1 and an inert non-toxic carrier thereof.

8. A pharmaceutical composition comprising as the active ingredient thereof, from about 1 to about 200 milligrams of a compound of claim 4 and an inert non-toxic carrier thereof.

9. A method of producing both Ca$^{2+}$-antagonistic action and adrenergic beta-receptor blocking activity by administering a compound of claim 1.

10. A method of treatment and prevention of ischemic heart-disease by administering a compound of claim 1.

* * * * *